United States Patent
Tsuji et al.

(10) Patent No.: US 9,346,044 B2
(45) Date of Patent: May 24, 2016

(54) COPPER-BASED CATALYST PRECURSOR, METHOD FOR MANUFACTURING SAME, AND HYDROGENATION METHOD

(71) Applicants: KURARAY CO., LTD., Kurashiki-shi (JP); SAKAI CHEMICAL INDUSTRY CO., LTD., Sakai-shi (JP)

(72) Inventors: Tomoaki Tsuji, Kamisu (JP); Keiichi Tabata, Sakai (JP); Toshihiro Sugaya, Sakai (JP); Akio Nakashima, Sakai (JP)

(73) Assignees: KURARAY CO., LTD., Kurashiki-shi (JP); SAKAI CHEMICAL INDUSTRY CO., LTD., Sakai-shi (JP)

( * ) Notice: Subject to any disclaimer, the term of this patent is extended or adjusted under 35 U.S.C. 154(b) by 0 days.

(21) Appl. No.: 14/425,469

(22) PCT Filed: Aug. 30, 2013

(86) PCT No.: PCT/JP2013/073378
§ 371 (c)(1),
(2) Date: Mar. 3, 2015

(87) PCT Pub. No.: WO2014/034879
PCT Pub. Date: Mar. 6, 2014

(65) Prior Publication Data
US 2015/0224492 A1    Aug. 13, 2015

(30) Foreign Application Priority Data
Sep. 3, 2012  (JP) .................................. 2012-193533

(51) Int. Cl.
| | | |
|---|---|---|
| B01J 37/03 | (2006.01) | |
| C07C 29/143 | (2006.01) | |
| B01J 37/08 | (2006.01) | |
| B01J 35/10 | (2006.01) | |
| B01J 23/00 | (2006.01) | |
| B01J 23/78 | (2006.01) | |
| C07C 29/17 | (2006.01) | |
| B01J 23/89 | (2006.01) | |
| B01J 37/04 | (2006.01) | |
| B01J 37/16 | (2006.01) | |

(52) U.S. Cl.
CPC .............. *B01J 37/031* (2013.01); *B01J 23/005* (2013.01); *B01J 23/78* (2013.01); *B01J 23/8946* (2013.01); *B01J 35/10* (2013.01); *B01J 35/1014* (2013.01); *B01J 35/1019* (2013.01); *B01J 37/03* (2013.01); *B01J 37/04* (2013.01); *B01J 37/08* (2013.01); *B01J 37/16* (2013.01); *C07C 29/143* (2013.01); *C07C 29/175* (2013.01); *B01J 2523/00* (2013.01)

(58) Field of Classification Search
CPC ........ B01J 23/78; B01J 35/1019; B01J 37/03; B01J 23/005; C07C 29/143
See application file for complete search history.

(56) References Cited

U.S. PATENT DOCUMENTS

| | | | |
|---|---|---|---|
| 4,144,198 A | 3/1979 | Miya et al. | |
| 4,252,689 A * | 2/1981 | Miya .................... | B01J 23/745 502/331 |
| 5,763,353 A * | 6/1998 | Kadono ................ | B01J 23/005 502/329 |
| 5,977,010 A | 11/1999 | Roberts et al. | |
| 2010/0030001 A1 | 2/2010 | Chen et al. | |
| 2012/0264976 A1 | 10/2012 | Harada et al. | |

FOREIGN PATENT DOCUMENTS

| | | |
|---|---|---|
| JP | 53 92395 | 8/1978 |
| JP | 55 8820 | 1/1980 |
| JP | 55 129151 | 10/1980 |
| JP | 2 218638 | 8/1990 |
| JP | 2 251245 | 10/1990 |
| JP | 4 22437 | 1/1992 |
| JP | 5 31366 | 2/1993 |
| JP | 5 168931 | 7/1993 |
| JP | 5 337371 | 12/1993 |
| JP | 6 226100 | 8/1994 |
| JP | 9 276699 | 10/1997 |
| JP | 11 171814 | 6/1999 |
| JP | 11 507867 | 7/1999 |
| JP | 2004 292202 | 10/2004 |
| JP | 2007 289855 | 11/2007 |
| JP | 2007289855 A * | 11/2007 |
| JP | 2008 247865 | 10/2008 |
| JP | 2011 529497 | 12/2011 |
| WO | 2011 078354 | 6/2011 |

OTHER PUBLICATIONS

International Search Report Issued Dec. 3, 2013 in PCT/JP13/073378 Filed Aug. 30, 2013.

* cited by examiner

*Primary Examiner* — Yong Chu
(74) *Attorney, Agent, or Firm* — Oblon, McClelland, Maier & Neustadt, L.L.P.

(57) ABSTRACT

A copper-based catalyst precursor capable of achieving a high conversion ratio and high selectivity in the isomerization reaction of a β,γ-unsaturated alcohol portion and a method for producing the same and to provide a hydrogenation method in which the copper-based catalyst precursor is used are provided. Specifically, a copper-based catalyst precursor obtained by calcining a mixture containing copper, iron, aluminum, and calcium silicate in which an atomic ratio of iron and aluminum to copper [(Fe+Al)/Cu] is in a range of 1.71 to 2.5, an atomic ratio of aluminum to iron [Al/Fe] is in a range of 0.001 to 3.3, and calcium silicate is contained in a range of 15% by mass to 65% by mass at a temperature in a range of 500° C. to 1,000° C. and a hydrogenation method in which the copper-based catalyst precursor is used are provided.

15 Claims, No Drawings

COPPER-BASED CATALYST PRECURSOR, METHOD FOR MANUFACTURING SAME, AND HYDROGENATION METHOD

TECHNICAL FIELD

The present invention relates to a copper-based catalyst precursor, a method for producing the same, and a hydrogenation method. In more detail, the present invention relates to a copper-based catalyst precursor containing copper, iron, aluminum, and the like, a method for producing the same, and a hydrogenation method in which the copper-based catalyst precursor is used. Furthermore, the present invention also relates to a copper-based catalyst obtained by reducing the copper-based catalyst precursor.

BACKGROUND ART

As a method for obtaining an aldehyde compound by isomerizing a $\beta,\gamma$-unsaturated alcohol portion, for example, an isomerization reaction of 7-octenal from 2,7-octadiene-1-ol is known. It has been reported that, in the isomerization reaction, the use of a copper-based catalyst precursor containing copper, iron, and aluminum enables the selective production of target substances (refer to PTL 1 to 3).

As a method for producing the copper-based catalyst precursor containing copper, iron, and aluminum, a method in which an aqueous solution of mixed metal salts including a water-soluble copper salt, a water-soluble iron salt, and a water-soluble aluminum salt as main components with a basic aqueous solution as a precipitant are reacted together so as to obtain a coprecipitate containing copper, iron, and aluminum, the coprecipitate is filtered, then, washed with water, dried, and calcined is known (refer to PTL 4 and 5).

When the coprecipitate containing copper, iron, and aluminum is calcined at a temperature in a range of 600° C. to 1,000° C., a spinel structure is formed. It is known that the atomic ratio between copper, iron, and aluminum in the coprecipitate is a factor that changes the dispersibility and the like of copper in the spinel structure, and furthermore, changes the activity and selectivity of the copper-based catalyst (refer to PTL 4 to 8).

It is also known that, in a case in which a copper-based catalyst precursor containing copper, iron, and aluminum which is obtained by coprecipitating a copper compound, an iron compound, and an aluminum compound on the surface of a carrier, and calcining the coprecipitate at 750° C. is used in a hydrogenation reaction, the activity and selectivity of the copper-based catalyst are changed depending on the kind of the carrier (PTL 9). That is, it is known that the atomic ratio between copper, iron, and aluminum in the coprecipitate, the kind and content of the carrier included in the coprecipitate, and the calcination temperature for turning the coprecipitate into the copper-based catalyst precursor change the activity and selectivity of the copper-based catalyst.

When the coprecipitate containing copper, iron, and aluminum is dried at a temperature in a range of 100° C. to 150° C., and then calcined at a temperature in a range of 600° C. to 1,000° C., a copper-based catalyst precursor can be obtained. Furthermore, when the copper-based catalyst precursor is hydrogen-reduced, the precursor becomes activated, and then can be used in desired reactions as a copper-based catalyst. Alternatively, it is also possible to crush the precursor after the calcining, activate the obtained powder-form copper-based catalyst precursor through hydrogen reduction, and use the powder in reactions as a powder-form copper-based catalyst. When it is also possible to use the calcined powder-form copper-based catalyst precursor formed through compression, extrusion, or the like as desired, it is also possible to use the dried coprecipitate that is formed through compression, extrusion, or the like, and then is calcined (refer to PLT 5, 12, and the like).

It is known that the copper-based catalyst precursor containing copper, iron, and aluminum can be used in a variety of hydrogenation reactions such as hydrogenation from an aliphatic ester compound to a higher alcohol (refer to PLT 4 to 12).

CITATION LIST

Patent Literature

[PTL 1] JP-A-02-218638
[PTL 2] JP-A-11-171814
[PTL 3] JP-A-20-247865
[PTL 4] JP-A-53-92395
[PTL 5] JP-A-55-8820
[PTL 6] JP-A-55-129151
[PTL 7] JP-A-2-251245
[PTL 8] JP-A-4-22437
[PTL 9] JP-A-5-31366
[PTL 10] JP-A-5-168931
[PTL 11] JP-A-9-276699
[PTL 12] JP-A-6-226100

SUMMARY OF INVENTION

Technical Problem

The present inventors prepared a copper-based catalyst through the hydrogen reduction of a copper-based catalyst precursor obtained by adding $\gamma$-alumina as a carrier, which is described to be preferable in PLT 11, to a coprecipitate containing copper, iron, and aluminum, washing the mixture, drying the obtained coprecipitate at 120° C., and then calcining the coprecipitate at an arbitrary temperature in a range of 120° C. to 800° C. As a result of using the copper-based catalyst in an isomerization reaction of 2,7-octadiene-1-ol to 7-octenal, it was found that, while the conversion ratio improved as the calcination temperature increased, the conversion ratio was still low and unsatisfactory, and furthermore, the selectivity was also low. In the isomerization reaction of 2,7-octadiene-1-ol to 7-octenal, particularly, it is difficult to separate the target substance of 7-octenal and a byproduct of 2,7-octadienal. As a result, there has been a desperate desire for the development of a copper-based catalyst capable of obtaining a high conversion ratio and increasing the selectivity of 7-octenal, even by a slight amount. In addition, it can be said that the copper-based catalyst is also useful as a hydrogenation catalyst capable of hydrogenating a carbon-carbon double bond or a carbon-oxygen double bond, and particularly, 1-octanol which is useful as a resin plasticizer can be produced using the hydrogenation reaction of 7-octenal.

Therefore, an object of the present invention is to provide a copper-based catalyst precursor capable of achieving a high conversion ratio and high selectivity in the isomerization reaction of a $\beta,\gamma$-unsaturated alcohol portion and a method for producing the same and to provide a hydrogenation method in which the copper-based catalyst precursor is used.

Solution to Problem

As a result of intensive studies, the present inventors found that a copper-based catalyst obtained from a copper-based catalyst precursor by adding calcium silicate to a coprecipitate containing copper, iron, and aluminum in which copper, iron, and aluminum have a relationship of a specific atomic ratio, filtering the obtained coprecipitate, and then calcining the coprecipitate at 800° C. improves the conversion ratio and the selectivity of 7-octenal in the isomerization reaction of 2,7-octadiene-1-ol to 7-octenal. It was found that this performance cannot be achieved only by optimizing the atomic ratio between copper, iron, and aluminum or the calcination temperature or only by using calcium silicate, but can be achieved by combining the options of the atomic ratio or the calcination temperature and the use of calcium silicate. Furthermore, it was found that the copper-based catalyst can also be used in the hydrogenation reaction of 1-octanol from 7-octenal.

In addition, it was found that, according to the production method, a decrease in the filtration rate during the filtration of a coprecipitated mixture, which is described in PTL 6 to 8, is not observed, and the production method is an industrially easy production method.

The present invention has been completed on the basis of the above-described findings.

That is, the present invention relates to the following [1] to [15].

[1] A copper-based catalyst precursor obtained by calcining a mixture containing copper, iron, aluminum, and calcium silicate in which an atomic ratio of iron and aluminum to copper [(Fe+Al)/Cu] is in a range of 1.71 to 2.5, an atomic ratio of aluminum to iron [Al/Fe] is in a range of 0.001 to 3.3, and calcium silicate is contained in a range of 15% by mass to 65% by mass at a temperature in a range of 500° C. to 1,000° C.

[2] The copper-based catalyst precursor according to [1], in which the mixture is a dried product of a coprecipitated mixture obtained by mixing a coprecipitate and calcium silicate, which coprecipitate is obtained by reacting a mixed aqueous solution including a water-soluble copper salt, a water-soluble iron salt, and a water-soluble aluminum salt with a basic aqueous solution.

[3] The copper-based catalyst precursor according to [1] or [2], in which, in the calcium silicate, an atomic ratio of silicon to calcium [Si/Ca] is in a range of 0.5 to 6.5.

[4] The copper-based catalyst precursor according to any one of [2] or [3], in which a BET specific surface area of the mixture is in a range of 50 m$^2$/g to 250 m$^2$/g.

[5] The copper-based catalyst precursor according to any one of [1] to [4], in which the calcium silicate is a Gyrolite-type synthetic calcium silicate represented by 2CaO.3SiO$_2$.mSiO$_2$.nH$_2$O (m and n, respectively, are numbers satisfying 1<m<2 and 2<n<3).

[6] The copper-based catalyst precursor according to [5], in which a bulk specific volume of the calcium silicate is 4 mL/g or more.

[7] A copper-based catalyst obtained by reducing the copper-based catalyst precursor according to any one of [1] to [6].

[8] A method for producing the copper-based catalyst precursor according to any one of [1] to [6], including:

first step: a step for generating a coprecipitate containing copper, iron, and aluminum by reacting a mixed aqueous solution including a water-soluble copper salt, a water-soluble iron salt, and a water-soluble aluminum salt with a basic aqueous solution;

second step: a step for obtaining a coprecipitated mixture by adding calcium silicate to a suspension including the coprecipitate obtained in the first step suspended in water and mixing the components together;

third step: a step for obtaining the dried product of the coprecipitated mixture by separating the coprecipitated mixture obtained in the second step, washing the coprecipitated mixture with water, and then drying the coprecipitated mixture; and fourth step: a step for calcining the dried product of the coprecipitated mixture obtained in the third step at a temperature in a range of 500° C. to 1,000° C.

[9] The method for producing the copper-based catalyst precursor according to [8], in which, in the first step, a reaction temperature is in a range of 5° C. to 150° C., and a pH of the aqueous solution is in a range of 6.0 to 13.5, and in the second step, a temperature of the suspension to which calcium silicate is added is in a range of 5° C. to 100° C., and a pH of the suspension is in a range of 7 to 9.

[10] The method for producing the copper-based catalyst precursor according to [8] or [9], in which, in the first step, the water-soluble copper salt is copper (II) sulfate, the water-soluble iron salt is iron (I) sulfate, and the water-soluble aluminum salt is aluminum sulfate.

[11] The method for producing the copper-based catalyst precursor according to any one of [8] to [10], in which a calcination temperature in the fourth step is in a range of 600° C. to 900° C.

[12] A hydrogenation method of a compound having either or both a carbon-carbon double bond and a carbon-oxygen double bond, in which the copper-based catalyst precursor according to any one of [1] to [6] is used.

[13] The hydrogenation method according to [12], in which the hydrogenation method is carried out at a temperature in a range of 100° C. to 300° C. and at a total pressure in a range of 0.01 MPa(G) to 30 MPa(G).

[14] The hydrogenation method according to [12] or [13], in which the hydrogenation method is carried out using a slurry-bed reaction method.

[15] The hydrogenation method according to any one of [12] to [14], in which the compound having either or both a carbon-carbon double bond and a carbon-oxygen double bond is selected from a group consisting of aldehydes which may include a carbon-carbon double bond, ketones which may include a carbon-carbon double bond, carboxylic acids which may include a carbon-carbon double bond, esters which may include a carbon-carbon double bond, acid anhydrides which may include a carbon-carbon double bond, and sugars which may include a carbon-carbon double bond.

Advantageous Effects of Invention

The copper-based catalyst obtained by hydrogen-reducing the copper-based catalyst precursor of the present invention is capable of achieving a high conversion ratio and high selectivity in the isomerization of a β,γ-unsaturated alcohol portion. Furthermore, the copper-based catalyst obtained from the copper-based catalyst precursor can also be used for the hydrogenation of a carbon-carbon double bond, a carbon-oxygen double bond, and the like.

In addition, according to the production method of the present invention, it is possible to produce the copper-based catalyst precursor in an easy industrial manner.

DESCRIPTION OF EMBODIMENTS

[Copper-Based Catalyst Precursor]

The present invention is a copper-based catalyst precursor obtained by calcining a mixture containing copper, iron, aluminum, and calcium silicate in which the atomic ratio of iron and aluminum to copper [(Fe+Al)/Cu] is in a range of 1.71 to 2.5, the atomic ratio of aluminum to iron [Al/Fe] is in a range of 0.001 to 3.3, and calcium silicate is contained in a range of 15% by mass to 65% by mass at a temperature in a range of 500° C. to 1,000° C.

In a case in which the atomic ratio of iron and aluminum to copper is less than 1.71, the diameters of copper crystals in the copper-based catalyst are increased, and a decrease in the catalyst activity per unit mass of copper, a decrease in the selectivity into the target substance caused by the large diameter of metal crystals, and a decrease in the catalyst activity over time due to the growth of metallic copper crystals are caused. On the other hand, in a case in which the atomic ratio of iron and aluminum to copper exceeds 2.5, the content of copper included per unit mass of the copper-based catalyst is decreased, and thus a desired catalyst activity cannot be achieved. Meanwhile, in a case in which the atomic ratio of aluminum to iron exceeds 3.3, the conversion ratio and the selectivity are decreased in the isomerization reaction of a compound having a β,γ-unsaturated alcohol portion to an aldehyde compound.

From the above-described viewpoint, [(Fe+Al)/Cu] is preferably in a range of 1.80 to 2.50, more preferably in a range of 1.90 to 2.5, still more preferably in a range of 1.90 to 2.4, and particularly preferably in a range of 2.1 to 2.21. In addition, from the above-described viewpoint, [Al/Fe] is preferably in a range of 0.001 to 3.2, more preferably in a range of 0.001 to 3.0, still more preferably in a range of 0.005 to 2.9, and particularly preferably in a range of 0.20 to 0.45.

A method for producing the copper-based catalyst precursor of the present invention will be described below.

As a method for producing the mixture, the following methods can be used.

(a) A method in which a coprecipitate obtained by reacting a mixed aqueous solution including a water-soluble copper salt, a water-soluble iron salt, and a water-soluble aluminum salt with a basic aqueous solution is mixed with calcium silicate. A method in which a suspension including the coprecipitate suspended in water and calcium silicate are mixed together is preferred.

(b) A method in which a coprecipitate is generated by reacting a mixed aqueous solution including a water-soluble copper salt, a water-soluble iron salt, and a water-soluble aluminum salt with a basic aqueous solution, the separated coprecipitate is dried, calcium silicate is added to the coprecipitate, and calcium silicate and the coprecipitate are mixed together in solid phases.

(c) A method in which a coprecipitate is generated by reacting a mixed aqueous solution including one or two selected from a water-soluble copper salt, a water-soluble iron salt, and a water-soluble aluminum salt with a basic aqueous solution, the coprecipitate, oxides or hydroxides of metals selected from copper, iron, and aluminum (the metals are selected so that three metals of copper, iron, and aluminum are all present in the mixture), and calcium silicate are mixed together, and the mixture is isolated and dried.

(d) A method in which oxides or hydroxides of metals of copper, iron, and aluminum and calcium silicate are mixed together in solid phases or liquid phases.

In any of the methods, other components may be further mixed in, and metals other than copper, iron, and aluminum may be included in the mixture.

The mixture or coprecipitated mixture obtained in the above-described manner is separated, and then dried, thereby obtaining the dried product of the coprecipitated mixture.

From the viewpoint of the uniform mixing of copper, iron, and aluminum and productivity, the method (a) is preferably employed. As copper, iron, and aluminum are more uniformly mixed together, it is possible to achieve the desired selectivity and activity of the copper-based catalyst with favorable reproducibility.

The copper-based catalyst precursor of the present invention is more preferably produced using a production method including first to fourth steps described below.

First step: a step for generating a coprecipitate containing copper, iron, and aluminum by reacting a mixed aqueous solution including a water-soluble copper salt, a water-soluble iron salt, and a water-soluble aluminum salt with a basic aqueous solution.

Second step: a step for obtaining a coprecipitated mixture by adding calcium silicate to a suspension including the coprecipitate obtained in the first step suspended in water and mixing the components together.

Third step: a step for obtaining the dried product of the coprecipitated mixture by separating the coprecipitated mixture obtained in the second step, washing the coprecipitated mixture with water, and then drying the coprecipitated mixture.

Fourth step: a step for calcining the dried product of the coprecipitated mixture obtained in the third step at a temperature in a range of 500° C. to 1,000° C.

Hereinafter, the respective steps will be sequentially described in detail.

(First Step)

The first step is a step for generating a coprecipitate containing copper, iron, and aluminum by reacting a mixed aqueous solution including a water-soluble copper salt, a water-soluble iron salt, and a water-soluble aluminum salt with a basic aqueous solution.

In the coprecipitate obtained in the first step, the atomic ratio of iron and aluminum to copper [(Fe+Al)/Cu] is preferably in a range of 1.71 to 2.5, and the atomic ratio of aluminum to iron [Al/Fe] is preferably in a range of 0.001 to 3.3. With the atomic ratios in the above-described ranges, it is possible to obtain the target copper-based catalyst precursor.

In the coprecipitate, [(Fe+Al)/Cu] is preferably in a range of 1.80 to 2.50, more preferably in a range of 1.90 to 2.5, still more preferably in a range of 1.90 to 2.4, and particularly preferably in a range of 2.1 to 2.21. In addition, [Al/Fe] is preferably in a range of 0.001 to 3.2, more preferably in a range of 0.001 to 3.0, still more preferably in a range of 0.005 to 2.9, and particularly preferably in a range of 0.20 to 0.45.

Meanwhile, regarding [(Fe+Al)/Cu] and [Al/Fe], it is possible to arbitrarily combine the above-described ranges.

Examples of the water-soluble copper salt include hydrosulfate, hydrogen sulfate, nitrate, carbonates, hydrogen carbonates, organic acid salts, chlorides, and the like of copper. More specific examples thereof include copper (II) sulfate, copper (II) nitrate, copper (II) chloride, and the like. The water-soluble copper salt may be singly used, or two or more water-soluble copper salts may be jointly used. From the viewpoint of easy procurement and price, copper (II) sulfate is preferred.

Examples of the water-soluble iron salt include hydrosulfate, hydrogen sulfate, nitrate, carbonates, hydrogen carbonates, organic acid salts, chlorides, and the like of iron. More specific examples thereof include iron (I) sulfate, iron (I) nitrate, iron (I) chloride, and the like. The water-soluble iron salt may be singly used, or two or more water-soluble iron salts may be jointly used. From the viewpoint of easy procurement and price, iron (I) sulfate is preferred.

Examples of the water-soluble aluminum salt include acetate, nitrate, hydrosulfate, and the like of aluminum. More specific examples thereof include sodium aluminate, aluminum sulfate, aluminum chloride, aluminum nitrate, and the like. The water-soluble aluminum salt may be singly used, or two or more water-soluble aluminum salts may be jointly used. From the viewpoint of easy procurement and price, aluminum sulfate is preferred.

The water-soluble copper salt, the water-soluble iron salt, and the water-soluble aluminum salt may contain a free acid that does not form a complex with metal, or may be a hydrate.

From the viewpoint of producing the homogeneous coprecipitate, an aqueous solution of the water-soluble copper salt, the water-soluble iron salt, and the water-soluble aluminum salt (hereinafter, in some cases, will be collectively referred to as metal salts) preferably includes no insoluble matter, and it is preferable to prepare a uniform solution through filtration if necessary.

There is no particular limitation regarding the concentration of the aqueous solution of the metal salts, but the concentration of the metal salts is preferably in a range of 5% by mass to 35% by mass, and more preferably in a range of 10% by mass to 25% by mass. When the concentration is 35% by mass or lower, it is difficult for a heterogeneous coprecipitate to be generated during the reaction with the basic aqueous solution. On the other hand, when the concentration is 5% by mass or higher, the volume efficiency is sufficient, and the production cost of the copper-based catalyst precursor can be reduced.

In a case in which the metal salts contain a free acid, the concentrations of the free acid included in the respective metal salts are all preferably in a range of 0.05% by mass to 20% by mass, and more preferably in a range of 0.1% by mass to 10% by mass. In the case of the metal salts containing 0.05% by mass or higher of the free acid, it is not necessary to purify the metal salts through crystallization in order to remove the free acid, and the production cost of the metal salts can be reduced. In addition, in a case in which the concentration of the free acid is 20% by mass or lower, a basic substance for neutralizing the free acid is not required, and there is no concern of catalyst performance being degraded by the interfusion of neutral salts produced from the free acid and the basic substance into the coprecipitate.

Examples of the basic substance for preparing the basic aqueous solution include hydroxides of alkali metals, hydroxides of alkali earth metals, carbonates of alkali metals, carbonates of alkali earth metals, hydrogen carbonates of alkali metals, hydrogen carbonates of alkali earth metals, and the like. More specific examples thereof include lithium hydroxide, sodium hydroxide, potassium hydroxide, sodium carbonate, sodium hydrogen carbonate, and the like. As the basic substance, additionally, an inorganic base such as ammonia or an organic base such as urea or ammonium carbonate can also be used.

The basic substance may be singly used, or two or more basic substances may be jointly used. From the viewpoint of easy procurement and price, sodium hydroxide is preferred.

The reaction temperature is preferably in a range of 5° C. to 150° C., and more preferably in a range of 60° C. to 100° C. When the reaction temperature is 5° C. or higher, the time taken to neutralize the free acid becomes short, and there is no concern of catalyst performance being degraded by the interfusion of alkali metal salts of acids and the like into the coprecipitate. In addition, when the reaction temperature is 150° C. or lower, a pressure-resistant container or the like is unnecessary, which is economically preferred.

Examples of a chemical mixing procedure for reacting an aqueous solution including the water-soluble copper salt, the water-soluble iron salt, and the water-soluble aluminum salt and the basic aqueous solution include (1) a method in which a variety of aqueous solutions of metal salts are added to the basic aqueous solution, (2) a method in which the basic aqueous solution is added to a variety of aqueous solutions of metal salts, and the like. From the viewpoint of controlling the reaction system to be basic, the method (1) is preferred.

The pH inside the reaction system is preferably in a range of 6.0 to 13.5, and more preferably in a range of 7.0 to 9.0. When the pH inside the reaction system is 6.0 or more, there are no cases in which the homogeneity of the coprecipitate is impaired by the re-dissolution of the copper component, and catalyst performance is not degraded. In addition, when the pH is 13.5 or less, there are no cases in which neutral salts generated from the basic substance interfuse into the coprecipitate, and there is no concern of catalyst performance being degraded.

When the coprecipitate having desired Cu/Fe/Al atomic ratios, that is, desired [(Fe+Al)/Cu] and desired [Al/Fe] is produced, it is preferable to prepare in advance a mixed aqueous solution obtained by mixing (preferably uniformly mixing) the water-soluble copper salt, the water-soluble iron salt, and the water-soluble aluminum salt so that desired metal atomic ratios are obtained, and add the mixed aqueous solution to the basic aqueous solution from the viewpoint of producing the homogeneous coprecipitate. For example, when the aluminum salt and the basic aqueous solution are reacted together, and then the copper salt, the iron salt, and the basic aqueous solution are reacted together, there are cases in which copper hydroxide and iron hydroxide accumulate using aluminum hydroxide as a nucleus, and thus a heterogeneous coprecipitate can be obtained. In a case in which the heterogeneous coprecipitate is calcined, a spinel structure made up of copper and iron is formed, and thus desired catalyst performance cannot be achieved.

The mixed aqueous solution prepared in the above-described manner is preferably added, that is, added gently dropwise to the basic aqueous solution. The dropwise addition time is preferably in a range of 30 minutes to 360 minutes, and more preferably in a range of 60 minutes to 240 minutes. When the dropwise addition time is 30 minutes or longer, the mixed aqueous solution is sufficiently stirred and mixed with the basic aqueous solution, and thus there are no cases in which temperature control becomes difficult due to reaction heat, and a heterogeneous coprecipitate is not easily generated. In addition, when the dropwise addition time is 360 minutes or shorter, the volume efficiency is sufficient, and the production cost of the copper-based catalyst precursor can be reduced.

There is no particular limitation regarding the state inside the reaction system; however, generally, a state in which a coprecipitate being generated does not settle, and is dispersed in the system is preferred. In a state in which the coprecipitate does not settle, a heterogeneous coprecipitate is not generated, and thus the performance of the copper-based catalyst improves.

In addition, it is normal to allow an aging time until the reaction is completed after the mixed aqueous solution is added dropwise to the basic aqueous solution, which is preferable. Generally, the aging time is preferably in a range of 1 hour to 10 hours. Meanwhile, the change in the pH of a suspension of the coprecipitate during aging is preferably less than 0.3 per hour.

While it is also possible to obtain the coprecipitated mixture by directly adding calcium silicate to the suspension including the coprecipitate obtained in the above-described manner, and then filtering the mixture, from the viewpoint of avoiding the interfusion of neutral salts into the coprecipitate, it is preferable to wash the coprecipitate, and then proceed to the second step described below. More specifically, it is preferable to obtain the coprecipitate after repeating an operation in which the suspension including the coprecipitate is left to stand at a temperature preferably in a range of 5° C. to 100° C., more preferably in a range of 10° C. to 80° C., and still more preferably in a range of 30° C. to 70° C., supernatant is removed using the decantation method, and then ion exchange water is added until the pH of the supernatant falls in a range of 7 to 9.

(Second Step)

The second step is a step for obtaining a coprecipitated mixture by adding calcium silicate to the suspension including the coprecipitate obtained in the first step suspended in water and mixing the components together.

As the suspension including the coprecipitate suspended in water, as described above, the suspension of the coprecipitate obtained immediately after the reaction in the first step may be used without any changes, or a suspension obtained by washing the coprecipitate obtained immediately after the reaction in the first step, and then adding water may be used. The pH of the suspension is preferably in a range of 7.0 to 9.0, and more preferably in a range of 7.0 to 8.0.

The temperature at which the suspension and calcium silicate are mixed together is preferably in a range of 5° C. to 100° C., more preferably in a range of 10° C. to 80° C., and still more preferably in a range of 30° C. to 70° C. In addition, the suspension and calcium silicate are preferably mixed in a state in which the suspension and calcium silicate are stirred so that the coprecipitate does not settle and accumulate.

In the calcium silicate being added, the atomic ratio of silicon to calcium [Si/Ca] is preferably in a range of 0.5 to 6.5, more preferably in a range of 1.6 to 4.0, and still more preferably in a range of 2.3 to 3.7. Meanwhile, an amount of calcium silicate is preferably added so that the content of calcium silicate included in the dried product of the mixture obtained in the third step described below falls in a range of 15% by mass to 65% by mass (more preferably in a range of 20% by mass to 55% by mass). When the content is 15% by mass or more, the filtration speed of the coprecipitated mixture made up of the coprecipitate and calcium silicate is sufficiently fast. In addition, when the content is 65% by mass or less, it is possible to maintain the content of copper in the copper-based catalyst at a high level, and there is no concern of catalyst activity being degraded.

Examples of calcium silicate used in the present invention include xonotite, tobermorite, gyrolite, foshagite, hillebrandite, and the like, and calcium silicate can be used in a form made up of one or more thereof. From the viewpoint of facilitating the quality stabilization of the copper-based catalyst precursor of the present invention, a chemical synthetic product is preferred.

From the viewpoint of an increase in the filtration speed, the improvement of catalyst formability, and an increase in the dynamic strength of a forming catalyst, particularly, synthetic calcium silicate belonging to a Gyrolite-type calcium silicate is preferably used, and a petal-shaped synthetic calcium silicate belonging to Gyrolite-type calcium silicates is more preferably used.

A method for producing the petal-shaped calcium silicate is described in JP-B-60-29643. That is, the petal-shaped calcium silicate can be obtained by reacting an aqueous silicate (for example, sodium silicate) and a water-soluble calcium salt (for example, calcium chloride) together at a temperature in a range of 150° C. to 250° C. under conditions in which the content of a solvent falls in a range of 5 parts by mass to 100 parts by mass of the obtained calcium silicate. In the petal-shaped calcium silicate that can be obtained in the above-described manner, the atomic ratio [Si/Ca] is generally in a range of 1.6 to 6.5, the bulk specific volume is 4 mL/g or more, the oil absorption amount is 2.0 mL/g or more, and the refractive index is in a range of 1.46 to 1.54.

In more detail, for example, an aqueous solution of sodium silicate and an aqueous solution of calcium chloride are mixed together at room temperature at the atmospheric pressure so that the atomic ratio [Si/Ca] reaches approximately 2.6, the mixture is introduced into an autoclave at a water ratio of 30, the components are reacted together at 200° C. for 5 hours, then, the reactant is filtered, washed with water, and dried, whereby petal-shaped calcium silicate represented by $2CaO.3SiO_2.2.20SiO_2.2.30$-$2.60H_2O$ can be obtained.

As the petal-shaped calcium silicate, for example, "FLO-RITE" manufactured by Tomita Pharmaceutical Co., Ltd. is commercially available. The petal-shaped calcium silicate is generally represented by $2CaO.3SiO_2.mSiO_2.nH_2O$ (m and n, respectively, are numbers satisfying $1<m<2$ and $2<n<3$). The shape of the petal-shaped calcium silicate can be confirmed through electron microscope observation, and generally, the shape and thickness of the petal shape can be confirmed through electron microscope observation at a magnification in a range of 3,000 times to 10,000 times. Particularly, from the viewpoint of an increase in the production speed of the copper-based catalyst precursor of the present invention, the improvement of formability, and an increase in the dynamic strength of a forming catalyst precursor, 5% by mass or more of calcium silicate being used is the petal-shaped calcium silicate.

Since the size, shape, and the like of the petal included in the petal-shaped calcium silicate somewhat differ depending on the kinds of raw materials used for the production of calcium silicate, the mixing ratio of raw materials, and production conditions, the size, shape, and the like cannot be ordinarily limited; however, generally, a majority of the petals have a round shape, an oval shape, or the like having an average lengthwise diameter in a range of 0.1 µm to 30 µm and a thickness in a range of 0.005 µm to 0.1 µm, and a majority of the petals have a shape similar to a rose petal. Calcium silicate having an atomic ratio [Si/Ca] of less than 1.6 does not have a petal shape, and has a tobermorite or xonotite-type crystal form. On the other hand, in calcium silicate having an atomic ratio [Si/Ca] of more than 6.5, both the bulk specific volume and the oil absorption amount become small, and there is no growth of petal-shaped calcium silicate observed. Generally, calcium silicate having an atomic ratio [Si/Ca] of 4.0 or less is most widely employed, which is the same as in the present invention.

(Third Step)

The third step is a step for obtaining the dried product of the coprecipitated mixture by separating the coprecipitated mixture obtained in the second step, washing the coprecipitated mixture with water, and then drying the coprecipitated mixture.

For the separation of the coprecipitated mixture obtained in the second step, an arbitrary well-known method can be applied; however, from the viewpoint of easy operation, the filtration method is preferably applied.

When the filtered substance is washed with distilled water, ion exchange water, or the like, impurities such as sodium sulfate can be removed.

Any drying methods can be used as long as water can be removed, and generally, the coprecipitated mixture is preferably dried at 100° C. or higher at the atmospheric pressure.

In a case in which there is a desire to extend the service life of the copper-based catalyst, it is possible to use means for adding inorganic salts of metals such as zinc, magnesium, barium, sodium, and potassium to the copper-based catalyst precursor. Generally, the atomic ratio of the metals to copper [metals/Cu] is preferably in a range of 0.1 to 3.0. When the atomic ratio is 0.1 or more, desired effects such as the extension of the service life of the copper-based catalyst can be developed. When the atomic ratio is 3.0 or less, there are no cases in which the durability of the copper-based catalyst is degraded.

For example, in a case in which at least one selected from magnesium and zinc is added, there is a method in which the aqueous solution of the hydrosulfate thereof is added to the aqueous solution of the metal acid salts in the first step, thereby obtaining a coprecipitate. In addition, in a case in which at least one selected from barium, sodium, and potassium is added, there is a method in which the aqueous solution of the hydroxide thereof is applied to the coprecipitated mixture separated in the second step, and then is dried.

The dried product of the coprecipitated mixture obtained in the above-described manner has a BET specific surface area, which is the nitrogen adsorption specific surface area measured according to "Determination Of The Specific Surface Area Of Powders (Solids) By Gas Adsorption Methods" described in JIS Z8830:2001, preferably in a range of 50 m2/g to 250 m2/g, more preferably in a range of 100 m2/g to 200 m2/g, and still more preferably in a range of 125 m2/g to 175 m2/g. When the BET specific surface area is 50 m2/g or more, an increase in the pore volume of the copper-based catalyst improves the catalyst activity. When the BET specific surface area is 250 m2/g or less, the coprecipitate and calcium silicate become uniformly mixed together, and the selectivity in a hydrogenation reaction or an isomerization reaction improves.

The determination of the atomic ratios of copper, iron, and aluminum and the determination of the content of calcium silicate in the mixture including copper, iron, aluminum, and calcium silicate, which is used in the production of the copper-based catalyst precursor of the present invention, are the determinations of the dried product of the coprecipitated mixture obtained in the third step, and are values based on the qualitative and quantitative analysis results of elements measured according to "General Rules for X-ray Fluorescence Analysis" described in JIS K 0119:2008.

The atomic ratios of copper, iron, and aluminum are computed from the respective content ratios of copper (II) oxide (CuO), iron (II) oxide ($Fe_2O_3$), and aluminum oxide ($Al_2O_3$) determined according to the present method. The sum of the content ratios of calcium oxide (CaO) and silicon dioxide ($SiO_2$) determined according to the present method is used as the content ratio of calcium silicate.

(Fourth Step)

The fourth step is a step for calcining the dried product of the coprecipitated mixture obtained in the third step at a temperature in a range of 500° C. to 1,000° C.

When the dried product is calcined and, if necessary, crushed, the copper-based catalyst precursor is obtained. At this stage, the copper-based catalyst precursor has a powder form, and hereinafter, there are cases in which the copper-based catalyst precursor will be referred to as the powder-form copper-based catalyst precursor.

The formed copper-based catalyst precursor (hereinafter, referred to as the formed copper-based catalyst precursor), which is easily used in a fixed-bed reaction, can be obtained by forming and then calcining the dried product of the coprecipitated mixture or by casting the powder-form copper-based catalyst precursor.

The calcination temperature is in a range of 500° C. to 1,000° C. In a case in which the calcination temperature is lower than 500° C., the spinel structure is not sufficiently formed, and thus the catalyst activity per unit weight of copper is low, and the catalyst activity significantly degrades over time. On the other hand, in a case in which the calcination temperature exceeds 1,000° C., the pore volume is decreased due to melting and fixing, the catalyst activity degrades, thus, the copper-based catalyst precursor is fixed to a calcination kiln, and the yield of the copper-based catalyst precursor is decreased. From the same viewpoint, the calcination temperature is more preferably in a range of 600° C. to 900° C., and still more preferably in a range of 700° C. to 900° C.

The dried product is preferably calcined in an air atmosphere, an oxygen atmosphere, a hydrogen atmosphere, or an inert gas atmosphere such as nitrogen or argon, and from the viewpoint of convenience, the dried product is more preferably calcined in an air atmosphere. In a case in which the dried product is calcined in a hydrogen atmosphere, there are cases in which catalyst performance is degraded due to the crystal growth (so-called sintering) of the copper metal, and thus caution is required.

The gas pressure during the calcining can be selected from the atmospheric pressure or higher. From the viewpoint of the convenience of an apparatus for producing the copper-based catalyst and the improvement in the formation speed of the spinel structure, the dried product is preferably calcined at the atmospheric pressure. The calcination time is not particularly limited; however, generally, is preferably in a range of 1 hour to 12 hours, more preferably in a range of 2 hours to 10 hours, and still more preferably in a range of 4 hours to 8 hours.

As a method for producing the formed copper-based catalyst precursor, a method in which additives such as a forming aid, a pore supplying agent, a strengthening agent, and a binder such as clay are added to the dried product of the coprecipitated mixture or the powder-form copper-based catalyst precursor, and the mixture is extruded or compressed can be preferably applied. The additives are used depending on the necessity of obtaining the desired viscosity of paste or the porosity of the formed copper-based catalyst precursor, and the amount of the additives used is preferably in a range of 0.5% by mass to 20% by mass, and more preferably in a range of 1% by mass to 10% by mass of the total mixture.

Examples of the forming aid include graphite, carbon black, talc, starch, polyacrylic acid, methyl cellulose, glycerin monostearate, glycerin monooleate, liquid paraffin, mineral oil, plant oil, stearic acid, magnesium stearate, potassium stearate, palmitic acid, magnesium palmitate, potassium palmitate, and the like. Examples of the pore supplying agent include graphite, organic polymer powder such as polypropylene, sugars, starch, cellulose, and the like. In addition, examples of a strengthening material such as inorganic fibers include glass fibers and the like.

The shape of the formed copper-based catalyst precursor may be any shape called a tablet, a 2 spoke ring, an extrusion, a pellet, a rib extrusion, a trilobe, and a ring; however, from the viewpoint of the suppression of catalyst pulverization during loading into a reaction tube, a tablet or a 2 spoke ring, which is a compressed product having a high crushing strength, is preferred. A tablet is more preferred since it is possible to increase the amount of the copper-based catalyst precursor loaded into the reaction tube, and the pressure loss at the reaction tube outlet is decreased. There is no particular limitation regarding the size of the tablet; however, when the tablet has a cylindrical shape, it is preferable that the diameter is in a range of 0.5 mm to 10 mm, and the thickness is in a range of 0.5 mm to 10 mm, and it is more preferable that the diameter is in a range of 1 mm to 4 mm, and the thickness is in a range of 1 mm to 4 mm. When the copper-based catalyst precursor becomes not too large, the contact efficiency of the matrix does not decrease, and the amount of the copper-based catalyst precursor loaded into the reaction tube does not decrease, and thus the volume efficiency tends to increase. On the other hand, when the copper-based catalyst precursor becomes not too small, there is no case in which the matrix drifts due to an increase in the pressure loss, and there is a tendency that an excessive temperature increase and side reactions are suppressed.

[Method for Using the Copper-Based Catalyst Precursor]

Hereinafter, a method for using the copper-based catalyst precursor (the powder-form copper-based catalyst precursor and the formed copper-based catalyst precursor) will be described.

The copper-based catalyst precursor of the present invention can be helpfully used in the isomerization reaction of a compound having a $\beta,\gamma$-unsaturated alcohol portion, the hydrogenation reaction of a compound having either or both a carbon-carbon double bond and a carbon-oxygen double bond, and the like.

However, copper included in the copper-based catalyst precursor is in a monovalent or divalent oxidation state, and thus, in a case in which the copper-based catalyst precursor is used in the above-described reactions and the like, the copper-based catalyst precursor does not sufficiently develop the catalyst function. Therefore, it is necessary to reduce the copper-based catalyst precursor in advance so that copper in the copper-based catalyst precursor becomes neutral or, when the above-described reactions are caused, create conditions in the reaction system so that copper is reduced.

A method for reducing the copper-based catalyst precursor without any solvents will be described. This method can be applied in a case in which, for example, the powder-form copper-based catalyst is used in a slurry-bed reaction method, a fluidized-bed reaction method, or a fixed-bed reaction method and in a case in which the formed copper-based catalyst is used in the fixed-bed reaction method.

In a case in which the powder-form or formed copper-based catalyst precursor is reduced without any solvents using reducing gas, there are cases in which the copper-based catalyst precursor generates heat. In this case, sintering by heat generation is accelerated, and thus it is also possible to use the copper-based catalyst precursor after diluting the copper-based catalyst precursor with glass beads, silica, alumina, silicon carbide, or the like for the purpose of reducing the concentration of the copper-based catalyst per unit volume and increasing the heat removal efficiency.

In the reduction, reducing gas such as hydrogen or carbon monoxide is preferably used. The reducing gas may be appropriately diluted with inert gas such as nitrogen, helium, or argon. It is usual and preferable to use hydrogen as the reducing gas and nitrogen as the inert gas for dilution.

The reducing temperature is preferably in a range of 100° C. to 800° C., and more preferably in a range of 150° C. to 250° C. When the reducing temperature is 100° C. or higher, water molecules generated due to the reduction of the copper-based catalyst precursor are sufficiently removed, the necessary reducing time becomes short, and the copper-based catalyst precursor is sufficiently reduced. On the other hand, the reducing temperature is 800° C. or lower, there is no concern of catalyst performance being degraded due to the sintering of copper.

The pressure of the reducing gas is preferably in a range of 0.01 MPa (G) to 1.9 MPa (G). Since a higher pressure of the reducing gas facilitates the proceeding of sintering, it is more preferable to reduce the copper-based catalyst precursor at a pressure close to the atmospheric pressure as much as possible.

There is no particular limitation regarding the flow rate of the reducing gas, but the gas hourly space velocity (GHSV), which is obtained by dividing the supply gas volume velocity (m³/hr) by the volume (m³) of a catalyst layer made of the copper-based catalyst precursor that may include a diluted substance, is preferably in a range of 50 hr$^{-1}$ to 20,000 hr$^{-1}$, and more preferably in a range of 100 hr$^{-1}$ to 10,000 hr$^{-1}$. When the gas hourly space velocity is 50 hr$^{-1}$ or more, the efficiency of removing moisture generated due to the reduction is high, and the necessary reducing time becomes short, and thus there is no concern of sintering by the heat storage of the copper-based catalyst. In addition, when the gas hourly space velocity is 20,000 hr$^{-1}$ or less, the amount of energy required to maintain the temperature of the catalyst layer is small, which is economically preferable.

The necessary reducing time appropriately varies depending on the reducing temperature and the like; however, generally, it is preferable to continue the reduction until at least one of the generation of water and the absorption of the reducing gas becomes unobservable.

Generally, it is preferable to install the copper-based catalyst obtained through the above-described reduction treatment in the same reaction tube and directly introduce the matrix into the copper-based catalyst, thereby promoting desired reactions from the viewpoint of avoiding risks such as the ignition of the copper-based catalyst and improving the productivity of the target substance.

Next, a method for reducing the copper-based catalyst precursor in a solvent will be described. This method can be applied in a case in which the powder-form copper-based catalyst is used in a slurry-bed reaction method.

The copper-based catalyst precursor is reduced after being immersed in a solvent that does not poison copper-based catalysts. There is no particular limitation regarding the solvent, and alcohols, ethers, hydrocarbons, and the like can be preferably used. Examples of the alcohols include methanol, ethanol, octanol, dodecanol, and the like. Examples of the ethers include tetrahydrofuran, dioxane, tetraethylene glycol dimethyl ether, and the like. Examples of the hydrocarbons include hexane, cyclohexane, decalin, liquid paraffin, and the like.

Examples of a reducing agent used for the reduction of the copper-based catalyst precursor include hydrogen, carbon monoxide, ammonia, hydrazine, formaldehyde, lower alcohols such as methanol, and the like. The reducing agent may be singly used, or a mixture of two or more reducing agents may be used. In addition, the reducing agent may be diluted using an inert gas such as nitrogen, helium, or argon before being used. It is usual and preferable to use hydrogen as the reducing agent and nitrogen as the inert gas for dilution.

The reducing temperature is preferably in a range of 100° C. to 800° C., and more preferably in a range of 100° C. to 300° C. When the reducing temperature is 100° C. or higher, water molecules generated due to the reduction of the copper-based catalyst precursor are sufficiently removed, the necessary reducing time becomes short, and the copper-based catalyst precursor is sufficiently reduced. On the other hand, the reducing temperature is 800° C. or lower, there is no concern of catalyst performance being degraded due to the sintering of copper.

In a case in which a reducing gas such as hydrogen, carbon monoxide, or ammonia is used, the pressure of the reducing gas is preferably in a range of 0.01 MPa (G) to 10 MPa (G). Since a higher pressure of the reducing gas facilitates the proceeding of sintering, it is more preferable to reduce the copper-based catalyst precursor at a pressure close to the atmospheric pressure as much as possible. Furthermore, it is more preferable to shorten the reduction time by bubbling the reducing gas in the suspension and efficiently removing water molecules generated due to the reduction.

The necessary reducing time is appropriately varied depending on the reducing temperature and the like; however, generally, it is preferable to continue the reduction until at least one of the generation of water and the absorption of the reducing gas becomes unobservable.

While it is also possible to separate the copper-based catalyst obtained through the above-described reduction treatment through filtration or the like and then introduce the copper-based catalyst into a desired reaction system, generally, it is preferable to introduce a reaction matrix into the suspension of the copper-based catalyst, thereby promoting desired reactions from the viewpoint of avoiding risks such as the ignition of the copper-based catalyst and improving the productivity of the target substance.

(Isomerization Reaction of a Compound Having a β,γ-Unsaturated Alcohol Portion)

An aldehyde compound can be produced using an isomerization reaction of a compound having a β,γ-unsaturated alcohol portion in which the copper-based catalyst precursor of the present invention is used. As described above, the copper-based catalyst precursor is used after being reduced.

The isomerization reaction can be caused in a liquid phase or a gas phase using a reaction method such as a slurry-bed reaction method, a fluidized-bed reaction method, or a fixed-bed reaction method. However, in a case in which the reaction system is exposed to a high temperature for a long period of time, aldehydes being generated are thermally unstable, and thus the fixed-bed reaction method is preferably used from the viewpoint of a concern of the generation of high-boiling point substances, the conversion ratio, and the selectivity. In addition, the isomerization reaction is preferably caused in a gas phase.

Hereinafter, an isomerization reaction method in which the fixed-bed reaction method is used will be specifically described, but the method for using the copper-based catalyst (precursor) is not limited thereto.

The scope of the "compound having a β,γ-unsaturated alcohol portion" which is a matrix of the present isomerization reaction includes compounds which have a —C=C—C—OH portion and have a total of 4 to 30 carbon atoms. Examples thereof include 2-butene-1-ol, 2-pentene-1-ol, 2-hexene-1-ol, 2-heptene-1-ol, 2-octene-1-ol, 2,7-octadiene-1-ol, 2-nonene-1-ol, 2-decene-1-ol, 3-phenyl-2-propene-1-ol, 4-phenyl-2-butene-1-ol, 5-phenyl-2-pentene-1-ol, 6-phenyl-2-hexene-1-ol, 7-phenyl-2-heptene-1-ol, 8-phenyl-2-octene-1-ol, 9-phenyl-2-nonene-1-ol, 10-phenyl-2-decene-1-ol, 2-methyl-2-butene-1-ol, 2-methyl-2-pentene-1-ol, 2-methyl-2-hexene-1-ol, 2-methyl-2-heptene-1-ol, 2-methyl-2-octene-1-ol, 2-methyl-2-nonene-1-ol, 2-methyl-2-decene-1-ol, 6-benzyl-2-cyclohexene-1-ol, 4-phenyl-1-vinyl-cyclohexane-1-ol, and the like. Among them, the copper-based catalyst precursor of the present invention is useful for the isomerization reaction of 2,7-octadiene-1-ol.

If desired, it is also possible to use a matrix diluted in a solvent that does not poison copper-based catalysts. There is no particular limitation regarding the solvent, and examples thereof include alcohols, ethers, and hydrocarbons. Examples of the alcohols include methanol, ethanol, octanol, dodecanol, 7-octene-1-ol, and the like. Examples of the ethers include tetrahydrofuran, dioxane, tetraethylene glycol dimethyl ether, and the like. Examples of the hydrocarbons include hexane, cyclohexane, decalin, liquid paraffin, and the like. In some cases, it is also possible to use water as the solvent.

In a case in which 7-octene-1-ol is used as the solvent among the above-described solvents, some of the 7-octene-1-ol is converted to 7-octenal in the isomerization reaction system, and thus the use of 7-octene-1-ol is preferred from the viewpoint of the improvement of productivity in a case in which 7-octenal is produced.

When a fixed-bed reactor loaded with the copper-based catalyst obtained through reduction is placed at a desired temperature and a desired pressure, and a compound having a β,γ-unsaturated alcohol portion and a gas mixture made up of an inert gas and a reducing gas or an inert gas are supplied to the fixed-bed reactor at the same time, the isomerization reaction of the compound having a β,γ-unsaturated alcohol portion proceeds, and an aldehyde compound can be produced.

From the viewpoint of producing the uniform gas flow, the fixed-bed reactor is preferably a reactor having a tubular structure, and when the temperature of the copper-based catalyst being uniformly controlled is taken into account, a reactor having a multitubular structure in which multiple reaction tubes are disposed in parallel is more preferred. A reaction tube having a round cross-sectional shape is generally used as the reaction tube. From the viewpoint of ease of a catalyst loading operation and the uniform loading of the copper-based catalyst, it is preferable to vertically dispose linear straight tubes.

The tube diameter is not particularly limited, but is preferably in a range of 15 mm to 50 mm, and more preferably in a range of 20 mm to 40 mm. When the tube diameter is 15 mm or more, it is possible to suppress an increase in the number of reaction tubes, and thus the production cost of the reactor can be reduced. In addition, when the tube diameter is 50 mm or less, it is possible to suppress the heat storage of the copper-based catalyst in the tube center portion, and thus the acceleration of catalyst deactivation, a sequential reaction, a runaway reaction, and the like can be suppressed.

There is no particular limitation regarding the length and number of the reaction tubes, and it is preferable to appropriately set the length and number of the reaction tubes in consideration of the production cost of the reactor, the amount of the copper-based catalyst required to achieve a desired producing capability, and the like. Generally, a method in which the fixed-bed multitubular reactor is used as a heat exchange reactor, jackets are provided at the outside of the reaction tubes loaded with the copper-based catalyst, and steam, heated oil, or the like is made to pass through the jackets, thereby controlling the reaction temperature is preferably employed. The state of the matrix in the reaction system may be any of a liquid state or a gas state; however, from the viewpoint of maintaining the matrix conversion ratio at a high level in order to allow the matrix molecules to diffuse into the inside of the copper-based catalyst and suppressing the degradation of the catalyst activity due to the carbonization and the like of the matrix and a product on the surface of the copper-based catalyst, the matrix is preferably in a gas state.

The reaction temperature is preferably in a range of 100° C. to 800° C. When the reaction temperature is 100° C. or higher, the reaction activation energy is sufficient, and thus sufficient productivity can be achieved. When the reaction temperature is 800° C. or lower, a decrease in the yield of the target substance due to the thermal decomposition of the matrix or the product is suppressed, and furthermore, there is no concern that productivity may be decreased by the carbide of the matrix or the product covering the surface of the copper-based catalyst or catalyst performance may be decreased by the sintering of copper. From the same viewpoint, the reaction temperature is preferably in a range of 100° C. to 500° C., more preferably in a range of 100° C. to 300° C., and still more preferably in a range of 150° C. to 250° C.

The reaction pressure is preferably in a range of 0.01 MPa (G) to 1.9 MPa (G) from the viewpoint of the easy control of pressure and the reduction of reaction facility cost. From the viewpoint of improving the productivity by increasing the diffusion efficiency of the matrix into the copper-based catalyst, it is more preferable to use the matrix in a gas phase, and it is more preferable to set the pressure close to 0.01 MPa (G) as much as possible.

Together with the matrix, an inert gas or a gas mixture made up of a reducing gas and an inert gas is supplied. In the gas mixture, the content of the reducing gas is preferably in a range of 0.05% by volume to 20% by volume, more preferably in a range of 0.1% by volume to 15% by volume, and still more preferably in a range of 0.1% by volume to 10% by volume.

The fixed-bed reactor may be any of a down-flow reactor in which the components are supplied from the upper portion of the reactor or an up-flow reactor in which the components are supplied from the lower portion of the reactor; however, from the viewpoint of steadily removing liquid-phase high-boiling point substances, which are reaction byproducts, outside the system, the down-flow reactor is preferred.

From the viewpoint of cheap prices, hydrogen gas is preferably used as the reducing gas, and nitrogen gas is preferably used as the inert gas. There is no particular limitation regarding the amount of hydrogen gas supplied, but the number of hydrogen molecules is desirably equal to or more than the number of oxygen molecules included in nitrogen gas and the matrix. Conversely, in a case in which the number of hydrogen molecules supplied is excessively large, the hydrogenation of the matrix proceeds, and thus the selectivity of the target substance is degraded. Furthermore, it is necessary to appropriately select the contact efficiency between the copper-based catalyst and reducing gas molecules depending on physical properties such as the shape of the copper-based catalyst being used and the molecule diffusion rate, and thus it is necessary adjust the amount of the matrix supplied, the amount of the gas mixture supplied, the content of the reducing gas included in the gas mixture, and the like so that desired reactions and desired reaction achievement are achieved.

Regarding the amount of hydrogen gas supplied together with the matrix, the molecular ratio (molar ratio) of the matrix to the hydrogen gas [matrix/hydrogen gas] is preferably in a range of 99/1 to 75/25, more preferably in a range of 99/1 to 80/20, and still more preferably in a range of 97/3 to 80/20. When the molecular ratio (molar ratio) [matrix/hydrogen gas] is too small, that is, the amount of the hydrogen gas is too great, there is a concern that the selectivity of the aldehyde compound may be decreased. From the viewpoint of suppressing the generation of a dehydrogenated compound being accelerated, it is preferable to prevent the molecular ratio (molar ratio) [matrix/hydrogen gas] from becoming too great, that is, prevent the amount of the hydrogen gas from becoming too small.

There is no particular limitation regarding the amount of the matrix supplied, but the weight hourly space velocity (WHSV), which is obtained by dividing the weight of the matrix supplied (kg/hr) by the weight of the copper-based catalyst precursor (kg), is preferably in a range of 0.05 hr$^{-1}$ to 20 hr$^{-1}$, and more preferably in a range of 0.1 hr$^{-1}$ to 10 hr$^{-1}$. When the weight hourly space velocity is 0.05 hr$^{-1}$ or more, the contact time between the matrix, the product, and the copper-based catalyst becomes short, and it is possible to suppress the generation of the condensate of the matrix or the product or a decrease in the yield of the target substance due to the carbonization of the matrix or the product. When the weight hourly space velocity is 20 hr$^{-1}$ or less, the amount of energy required to maintain the temperature of the catalyst layer is small, which is economically preferable.

There is no particular limitation regarding the flow rate of the inert gas or the gas mixture, but the gas hourly space velocity (GHSV), which is obtained by dividing the supply gas volume velocity (m$^3$/hr) by the volume (m$^3$) of the catalyst layer made of the copper-based catalyst precursor that may include a diluted substance, is preferably in a range of 50 hr$^{-1}$ to 20,000 hr$^{-1}$, and more preferably in a range of 100 hr$^{-1}$ to 10,000 hr$^{-1}$. When the gas hourly space velocity is 50 hr$^{-1}$ or more, there is no concern of sintering due to the heat storage of the copper-based catalyst. In addition, when the gas hourly space velocity is 10,000 hr$^{-1}$ or less, the amount of energy required to maintain the temperature of the catalyst layer is small, which is economically preferable.

When the product discharged together with gas is liquefied using an agglomerating device, and is distilled at the atmospheric pressure or reduced pressure, it is possible to separate and purify the aldehyde compound which is the target substance.

When the reaction is continuously caused, there are cases in which the degradation of the catalyst activity is observed. In this case, the copper-based catalyst may be used after the copper-based catalyst used in the reaction is appropriately fired in the air or an oxygen atmosphere under pressurization in a range of 0.01 MPa (G) to 1.9 MPa (G) at a temperature in a range of the reaction temperature to 800° C. so as to carbonize organic compounds attached to the surface of the copper-based catalyst, the carbonized organic compounds are removed, and then the reduction treatment is carried out again.

(Hydrogenation Reaction of the Compound Having a Carbon-Carbon Double Bond or a Carbon-Oxygen Double Bond)

When the copper-based catalyst precursor of the present invention is used, it is possible to efficiently cause the hydrogenation reaction of the compound having either or both a carbon-carbon double bond and a carbon-oxygen double bond.

The hydrogenation reaction of a compound having a carbon-carbon double bond and a carbon-oxygen double bond can be caused using any reaction method of a slurry-bed reaction method, a fluidized-bed reaction method, and a fixed-bed reaction method. In a case in which the hydrogenation reaction is caused using the fixed-bed reaction method, the reaction can be caused under the same conditions as the isomerization reaction conditions for the compound having a β,γ-unsaturated alcohol portion except for the fact that the content of the hydrogen gas included in the gas mixture is preferably selected from a range of 1% by volume to 100% by volume, more preferably selected from a range of 50% by volume to 100% by volume, and still more preferably selected from a range of 80% by volume to 100% by volume.

Hereinafter, a hydrogenation reaction in which the slurry-bed reaction method is used will be specifically described, but the method for using the copper-based catalyst is not limited thereto.

The scope of the "compound having a carbon-carbon double bond" which is a matrix of the present hydrogenation reaction includes all compounds having a —C═C— portion. In the concept of the carbon-carbon double bond, double bonds formed by adding a carbon-carbon triple bond are also included.

In addition, the scope of the "compound having a carbon-oxygen double bond" which is another matrix of the present hydrogenation reaction includes all compounds having a —(C=O)— portion, and examples thereof include aldehydes, ketones, carboxylic acids, esters, acid anhydrides, sugars, and the like. In addition, compounds having a plurality of the above-described portion in a molecule are also included.

The matrix of the present hydrogenation reaction is preferably selected from the group consisting of aldehydes which may include a carbon-carbon double bond, ketones which may include a carbon-carbon double bond, carboxylic acids which may include a carbon-carbon double bond, esters which may include a carbon-carbon double bond, acid anhydrides which may include a carbon-carbon double bond, and sugars which may include a carbon-carbon double bond. In addition, from the viewpoint of the easy separation of the product, the matrix of the present hydrogenation reaction is preferably a compound having a total of 4 to 30 carbon atoms in a molecule, more preferably a compound having a total of 4 to 20 carbon atoms in a molecule, and still more preferably a compound having a total of 4 to 10 carbon atoms in a molecule.

Examples of the compounds having a carbon-carbon double bond include unsaturated aliphatic hydrocarbons, unsaturated aliphatic group-containing aromatic hydrocarbons, alicyclic olefin-based hydrocarbons, olefins having a functional group, and the like.

Examples of the unsaturated aliphatic hydrocarbons include ethylene, propylene, 1-butene, 1-pentene, 1-hexene, 1-heptene, 1-octene, 1-nonene, 2-butene, isobutene, 2-octene, 1,7-octadiene, vinyl cyclohexene, cyclooctadiene, dicyclopentadiene, butadiene polymers, isoprene polymers, and the like. Examples of the unsaturated aliphatic group-containing aromatic hydrocarbons include styrene, α-methylstyrene, β-methylstyrene, alkyl group nucleus-substituted styrene, divinyl benzene, and the like. Examples of the alicyclic olefin-based hydrocarbons include cyclopentene, cyclohexene, 1-methylcyclohexene, cyclooctene, limonene, and the like. Examples of the olefins having a functional group include allyl alcohol, crotyl alcohol, 3-methyl-3-butene-1-ol, 7-octene-1-ol, 2,7-octadienol, vinyl acetate, allyl acetate, methyl acrylate, ethyl acrylate, methyl methacrylate, allyl acrylate, vinyl methyl ether, allyl ethyl ether, 5-hexeneamide, acrylonitrile, 7-octenal, and the like.

In addition, there are also natural compounds having a carbon-carbon double bond, and examples of the natural compounds include vegetable oil such as soybean oil, canola oil, sunflower seed oil, cotton oil, earthnut oil, sesame oil, palm oil, palm kernel oil, flaxseed oil, castor oil, or coconut oil; animal oil such as beef fat, fish oil, or lard; unsaturated aliphatic acids obtained therefrom, and the like.

Among them, the copper-based catalyst precursor of the present invention is useful for the hydrogenation reaction of 7-octenal.

Specific examples of aldehydes, ketones, carboxylic acids, esters, acid anhydrides, and sugars as the compounds having a carbon-oxygen double bond will be described below.

Examples of the aldehyde compounds include formaldehyde, propionaldehyde, n-butylaldehyde, isobutylaldehyde, valeraldehyde, 2-methyl butylaldehyde, 3-methyl butylaldehyde, 2,2-dimethyl propionaldehyde, capronaldehyde, 2-methyl valeraldehyde, 3-methyl valeraldehyde, 4-methyl valeraldehyde, 2-ethyl butylaldehyde, 2,2-dimethyl butylaldehyde, 3,3-dimethyl butylaldehyde, caprilaldehyde, capric aldehyde, glutardialdehyde, 7-octenal, and the like.

Furthermore, the aldehyde compounds may be hydroxyaldehyde compounds having a hydroxyl group in the molecule, and examples thereof include 3-hydroxypropanal, dimethylol ethanal, trimethylol ethanal, 3-hydroxybutanal, 3-hydroxy-2-ethylhexanal, 3-hydroxy-2-methylpentanal, 2-methylolpropanal, 2,2-dimethylolpropanal, 3-hydroxy-2-methylbutanal, 3-hydroxypentanal, 2-methylolbutanal, 2,2-dimethylolbutanal, hydroxypivalic aldehyde, and the like.

Examples of the ketone compounds include acetone, butanone, 2-pentanone, 4-methyl-2-pentanone, 2-hexanone, cyclohexanone, isoboron, methyl isobutyl ketone, mesityl oxide, acetophenone, propiophenone, benzophenone, benzalactone, dibenzalactone, benzalactophenone, 2,3-butadion, 2,4-pentadion, 2,5-hexadion, 5-methyl vinyl ketone, and the like.

Among them, the copper-based catalyst precursor of the present invention is useful for the hydrogenation reaction of 4-methyl-2-pentanone.

Examples of the carboxylic acids include formic acid, acetic acid, propionic acid, butyric acid, isobutyric acid, n-valeric acid, trimethylacetic acid, caproic acid, enanthylic acid, capric acid, lauric acid, myristic acid, palmitic acid, stearic acid, acrylic acid, methacrylic acid, oleic acid, elaidic acid, linoleic acid, linolenic acid, cyclohexane carboxylic acid, benzoic acid, phenylacetic acid, ortho-toluic acid, meta-toluic acid, para-toluic acid, ortho-chlorobenzoic acid, para-chlorobenzoic acid, ortho-nitrobenzoic acid, para-nitrobenzoic acid, salicylic acid, para-hydroxybenzoic acid, anthranilic acid, para-aminobenzoic acid, oxalic acid, maleic acid, glutaric acid, adipic acid, pimelic acid, suberic acid, azelaic acid, sebacic acid, maleic acid, fumaric acid, isofumaric acid, terephthalic acid, 1,2-cyclohexane dicarboxylic acid, 1,4-cyclohexane dicarboxylic acid, and the like.

Furthermore, the carboxylic acids may be esterified compounds made up of a carboxylic acid and an alcohol, and the alcohol component constituting the ester is not particularly limited; however, the alcohol component is generally an aliphatic or alicyclic alcohol having 1 to 6 carbon atoms, and examples thereof include methanol, ethanol, propanol, butanol, pentanol, hexanol, cyclohexanol, and the like. Furthermore, lactones as esters cyclized in the molecule, for example, γ-butyrolactone, δ-valerolactone, and ε-caprolactone are also included.

If desired, it is also possible to use a matrix diluted in a solvent that does not poison copper-based catalysts. There is no particular limitation regarding the solvent, and examples thereof include alcohols, ethers, and hydrocarbons. Examples of the alcohols include methanol, ethanol, octanol, dodecanol, and the like. Examples of the ethers include tetrahydrofuran, dioxane, tetraethylene glycol dimethyl ether, and the like. Examples of the hydrocarbons include hexane, cyclohexane, decalin, liquid paraffin, and the like. In some cases, it is also possible to use at least one selected from water, matrixes, and products as the solvent.

The slurry-bed reaction method can be selected from two methods of a batch method (including a half continuous method) and a flow continuous method, and the flow continuous method in which the copper-based catalyst is easily collected and used is preferred. Hereinafter, the slurry-bed reaction method in which the flow continuous method is used will be briefly described.

When a slurry-bed reactor loaded with a suspension obtained through the reduction treatment of the copper-based catalyst precursor is placed at a desired temperature and a desired pressure, and a compound having either or both a carbon-carbon double bond and a carbon-oxygen double bond and hydrogen gas are supplied, hydrogenation can be caused.

Since a decrease in the size of the powder-form copper-based catalyst precursor increases the specific area per unit weight, the catalyst activity per unit mass of the copper-based catalyst becomes high. On the other hand, an increase in the size facilitates filtration after the reaction. From such a viewpoint, generally, a powder-form copper-based catalyst precursor screened with a mesh in a range of 16 to 400 is preferably used. The concentration of the powder-form copper-based catalyst included in the suspension is preferably in a range of 0.01% by mass to 50% by mass, and, from the viewpoint of the productivity per unit time and the properties of the powder-form copper-based catalyst being removed by filtration, is more preferably in a range of 1% by mass to 10% by mass.

The hydrogenation reaction temperature is preferably in a range of 100° C. to 800° C., more preferably in a range of 100° C. to 300° C., and still more preferably in a range of 150° C. to 250° C. When the reaction temperature is 100° C. or higher, the reaction activation energy becomes sufficient, and sufficient productivity can be achieved. In addition, when the reaction temperature is 800° C. or lower, a decrease in the yield of the target substance due to the thermal decomposition of the matrix and the product is suppressed, and furthermore, the degradation of productivity due to the surfaces of the copper-based catalyst covered with the carbide of the matrix or the product or the degradation of catalyst performance due to the sintering of copper is suppressed.

Generally, the hydrogen pressure is preferably selected from a range of 1 MPa (G) to 30 MPa (G). In the hydrogenation reaction in which the slurry-bed method is used, an increase in the hydrogen pressure increases the number of hydrogen molecules being dissolved in the solvent, and accordingly, the reaction rate improves, and therefore the pressure is preferably high even in the above-described hydrogen pressure range.

For the separation of the liquid-phase product and the copper-based catalyst, a method such as decantation or filtration can be employed. The separated copper-based catalyst that has been used before can be reused by washing the copper-based catalyst using an alcohol, an ether, a hydrocarbon solvent, or the like, then, bringing the copper-based catalyst into contact with the air, and carrying out calcination and the reducing treatment on the copper-based catalyst. The target substance can be separated and purified by distilling a liquid from which the copper-based catalyst has been separated in the atmosphere or at a reduced pressure.

EXAMPLES

Hereinafter, the present invention will be described in more detail using examples, but the present invention is not limited to the examples by any means.

The method for producing the copper-based catalyst precursor in the present invention will be described in detail in Examples 1 to 7. In addition, a method for producing a catalyst precursor for comparing catalyst performance will be described in detail in Reference Examples 1 to 5.

The atomic ratios of Cu, Fe, and Al and the content (% by mass) of calcium silicate are values based on the qualitative and quantitative analysis results of the elements measured from the dried product of the coprecipitated mixture obtained in the third step according to "General Rules for X-ray Fluorescence Analysis" described in JIS K 0119:2008 using a tube-above wavelength dispersive X-ray fluorescence spectrometer "ZSX Primus II" manufactured by Rigaku Corporation. The Cu/Fe/Al atomic ratios were computed from the content (% by mass) of copper (II) oxide (CuO), the content (% by mass) of iron (II) oxide ($Fe_2O_3$), and the content (% by mass) of aluminum oxide ($Al_2O_3$) determined according to the present method, and furthermore, (Fe+Al)/Cu and Al/Fe were obtained. The sum of the content (% by mass) of calcium oxide (CaO) and the content (% by mass) of silicon oxide ($SiO_2$) determined according to the present method was used as the content (% by mass) of calcium silicate.

In addition, the BET specific surface area is a value based on the nitrogen adsorption specific surface area measured from the dried product of the coprecipitated mixture obtained in the third step according to "Determination Of The Specific Surface Area Of Powders (Solids) By Gas Adsorption Methods" described in JIS Z8830:2001 using "GEMINI VII2390" manufactured by Micromeritics Japan.

In the respective examples described below, unless particularly otherwise described, ion exchange water was used as water, and operation were carried out in an air atmosphere having the atmospheric pressure.

Example 1

17.5 g (0.178 mol) of sulfuric acid, 94.2 g of copper (II) sulfate pentahydrate (0.377 mol of copper atom), 170.8 g of iron (I) sulfate heptahydrate (0.614 mol of iron atom), and 132.6 g of liquid aluminum sulfate (containing 8% of $Al_2O_3$) (0.208 mol of aluminum atom) were sequentially added to 2,000 g of water in a 5 L glass beaker including a stirrer and a heating device, were sufficiently stirred so as to prepare a uniform aqueous solution of metal sulfate, and the aqueous solution was heated to 50° C., and was maintained.

120 g of sodium hydroxide was dissolved in 2,000 g of water in a 10 L glass beaker including a stirrer and a heating device, and the solution was heated to 80° C. In a state in which the mixture was being stirred so as to prevent a coprecipitate from settling and accumulating even after the completion of the dropwise addition of the aqueous solution of metal sulfate, the aqueous solution of metal sulfate was added dropwise to an aqueous solution of sodium hydroxide using a metering pump over 120 minutes. At this time, the heating device was controlled so that the temperature of the reaction solution was maintained at 80° C.

After the completion of the dropwise addition, the aqueous solution mixture was aged for 1 hour at the same temperature in the same stirring state. After that, the aqueous solution mixture was cooled to 50° C., and was left to stand. Supernatant was removed through decantation, 4,000 g of first washing water was added, and the coprecipitate was stirred at 50° C., thereby washing the coprecipitate. This operation was repeated, and it was confirmed that the pH of the supernatant was 7.7 after the injection of fifth washing water. In a state in which the fifth washing water was present and the coprecipitate was being stirred at 50° C. so as to prevent the settlement of the coprecipitate, 75.0 g of calcium silicate (manufactured by Tomita Pharmaceutical Co., Ltd., "FLORITE") was added, and the mixture was aged for 1 hour. The coprecipitated mixture was filtered at room temperature, and was dried in the air at 120° C. for 16 hours. The dried product of the obtained coprecipitated mixture was calcined at 800° C. in the air having the atmospheric pressure for 6 hours, thereby obtaining a powder-form copper-based catalyst precursor. The powder-form copper-based catalyst precursor obtained in the above-described manner will be referred to as a catalyst precursor A.

Example 2

The same operation was carried out in Example 1 except for the fact that sulfuric acid (17.5 g, 0.178 mol), copper (II) sulfate pentahydrate (94.2 g, 0.377 mol of copper atom), iron (I) sulfate heptahydrate (113.9 g, 0.410 mol of iron atom), and liquid aluminum sulfate (215.8 g, 0.339 mol of aluminum atom) were sequentially added so as to prepare a uniform aqueous solution of metal sulfate, and 86.7 g of calcium silicate (manufactured by Tomita Pharmaceutical Co., Ltd., "FLORITE") was added. The powder-form copper-based catalyst precursor obtained in the above-described manner will be referred to as a catalyst precursor B.

Example 3

The same operation was carried out in Example 1 except for the fact that sulfuric acid (17.5 g, 0.178 mol), copper (II) sulfate pentahydrate (94.2 g, 0.377 mol of copper atom), iron (I) sulfate heptahydrate (227.7 g, 0.819 mol of iron atom), and liquid aluminum sulfate (7.1 g, 0.011 mol of aluminum atom) were sequentially added so as to prepare a uniform aqueous solution of metal sulfate, and 70.2 g of calcium silicate (manufactured by Tomita Pharmaceutical Co., Ltd., "FLORITE") was added. The powder-form copper-based catalyst precursor obtained in the above-described manner will be referred to as a catalyst precursor C.

Example 4

The same operation was carried out in Example 1 except for the fact that sulfuric acid (17.5 g, 0.178 mol), copper (II) sulfate pentahydrate (94.2 g, 0.377 mol of copper atom), iron (I) sulfate heptahydrate (57.0 g, 0.205 mol of iron atom), and liquid aluminum sulfate (396.5 g, 0.622 mol of aluminum atom) were sequentially added so as to prepare a uniform aqueous solution of metal sulfate, and 89.4 g of calcium silicate (manufactured by Tomita Pharmaceutical Co., Ltd., "FLORITE") was added. The powder-form copper-based catalyst precursor obtained in the above-described manner will be referred to as a catalyst precursor D.

Example 5

The same operation was carried out in Example 2 except for the fact that the calcination temperature was changed to 600° C., and a powder-form copper-based catalyst precursor was obtained. The powder-form copper-based catalyst precursor obtained in the above-described manner will be referred to as a catalyst precursor E.

Example 6

The same operation was carried out in Example 1 except for the fact that 42.7 g of calcium silicate (manufactured by Tomita Pharmaceutical Co., Ltd., "FLORITE") was added. The powder-form copper-based catalyst precursor obtained in the above-described manner will be referred to as a catalyst precursor F.

Example 7

The same operation was carried out in Example 1 except for the fact that 24.9 g of calcium silicate (manufactured by Tomita Pharmaceutical Co., Ltd., "FLORITE") was added. The powder-form copper-based catalyst precursor obtained in the above-described manner will be referred to as a catalyst precursor G.

Hereinafter, a method for preparing the powder-form copper-based catalyst precursor for comparing the catalyst performance of the copper-based catalyst precursor of the present invention will be described as reference examples.

Copper-based catalyst precursors described in Reference Examples 1 to 3 can be prepared in the same manner as a catalyst precursor B; however, γ-alumina was added to the copper-based catalyst precursors instead of calcium silicate, and the copper-based catalyst precursors are intended to exhibit the availability of calcium silicate as a carrier. The copper-based catalyst precursor described in Reference Example 4 could be prepared in the same manner as the catalyst precursor B, but the calcination temperature was set to 400° C., and the copper-based catalyst precursor was used to clarify the influence of the calcination temperature. The copper-based catalyst precursor described in Reference Example 5 rarely included iron, and was used to clarify the necessity of iron.

Reference Example 1

The same operation was carried out in Example 2 except for the fact that 86.7 g of γ-alumina (manufactured by C. I. Kasei Co., Ltd., "NanoTek $Al_2O_3$") was added instead of 86.7 g of calcium silicate (manufactured by Tomita Pharmaceutical Co., Ltd., "FLORITE"). The powder-form copper-based catalyst precursor obtained in the above-described manner will be referred to as a catalyst precursor H1.

Reference Example 2

The same operation was carried out in Reference Example 1 except for the fact that the calcination temperature was changed to 600° C., and a powder-form copper-based catalyst precursor was obtained. The powder-form copper-based catalyst precursor obtained in the above-described manner will be referred to as a catalyst precursor H2.

Reference Example 3

The same operation was carried out in Reference Example 1 except for the fact that the calcination temperature was changed to 400° C., and a powder-form copper-based catalyst precursor was obtained. The powder-form copper-based catalyst precursor obtained in the above-described manner will be referred to as a catalyst precursor H3.

Reference Example 4

The same operation was carried out in Example 2 except for the fact that the calcination temperature was changed to 600° C., and a powder-form copper-based catalyst precursor was obtained. The powder-form copper-based catalyst precursor obtained in the above-described manner will be referred to as a catalyst precursor I.

Reference Example 5

The same operation was carried out in Example 1 except for the fact that sulfuric acid (17.5 g, 0.178 mol), copper (II) sulfate pentahydrate (94.2 g, 0.377 mol of copper atom), and liquid aluminum sulfate (471.3 g, 0.740 mol of aluminum atom) were sequentially added so as to prepare a uniform aqueous solution of metal sulfate, and 95.8 g of calcium silicate (manufactured by Tomita Pharmaceutical Co., Ltd., "FLORITE") was added. The powder-form copper-based catalyst precursor obtained in the above-described manner will be referred to as a catalyst precursor J.

Table 1 describes the analysis values of the dried products of the coprecipitated mixtures prepared in Examples 1 to 7 and Reference Examples 1 to 5.

For the copper-based catalyst precursors except for the copper-based catalyst precursors of Reference Examples 1 to 3, the Cu/Fe/Al atomic ratios are values computed from the component analysis values of the dried products of the coprecipitated mixtures, and the amount of calcium silicate is the sum of the % by mass of calcium oxide and silicon oxide in the analysis values of the dried products of the coprecipitated mixture. Meanwhile, for the copper-based catalyst precursors described in Reference Examples 1 to 3, the Cu/Fe/Al atomic ratios of the coprecipitates are values separately computed from the component analysis values of the Cu/Fe/Al atomic ratios of the dried products of the coprecipitates, and the % by mass of γ-alumina which was used as the additive during filtration was computed from the difference in component analysis value between the dried products and the coprecipitates. That is, since γ-alumina was added to the coprecipitates, the dried products of the present coprecipitated mixtures, substantially, had a Cu/Fe/Al atomic ratio of 1/1.10/0.93, and included 47.6% by mass of γ-alumina.

inside, a gas supply opening in the upper portion, and a sampling opening in the lower portion. The weight of the copper-based catalyst precursor A included in the diluted mixture was 26.5 g.

In a state in which the temperature of the catalyst layer was maintained in a range of 200±5° C., the air was circulated at 12 L/hr for 1 hour. After that, the supply of the air was stopped, and nitrogen gas was circulated at 137.5 L/hr for 1 hour so that the temperature of the catalyst layer was maintained in a range of 200±5° C. After that, the flow rate of hydrogen gas was increased while the flow rate of nitrogen gas was decreased so that the temperature of the catalyst layer was maintained in a range of 200±5° C., finally, the flow rate of hydrogen gas was set to 6 L/hr, and the copper-based catalyst precursor A was reduced over 1 hour.

After the reduction treatment, the supply of the hydrogen gas was stopped, and nitrogen gas and 2,7-octadiene-1-ol were circulated at 137.5 L/hr and 70.2 g/hr (0.558 mol/hr) respectively so that the temperature of the catalyst layer was

TABLE 1

| | Copper-based catalyst precursor | Analysis results | | | | | | | | | Calcination temperature (° C.) |
| --- | --- | --- | --- | --- | --- | --- | --- | --- | --- | --- | --- |
| | | CuO | $Fe_2O_3$ | $Al_2O_3$ | CaO | $SiO_2$ | Cu/Fe/Al | (Fe + Al)/Cu | Al/Fe | Calcium silicate (% by mass) | BET specific surface area ($m^2/g$) | |
| Example 1 | A | 18.0 | 29.0 | 6.8 | 13.4 | 31.7 | 1/1.61/0.59 | 2.2 | 0.37 | 45.1 | 130.5 | 800 |
| Example 2 | B | 18.2 | 18.7 | 10.9 | 13.7 | 37.6 | 1/1.02/0.93 | 1.95 | 0.91 | 51.3 | 151.8 | 800 |
| Example 3 | C | 18.3 | 40.5 | 0.2 | 11.8 | 27.9 | 1/2.20/0.02 | 2.22 | 0.01 | 39.7 | 168.4 | 800 |
| Example 4 | D | 19.1 | 10.4 | 18.0 | 13.9 | 37.5 | 1/0.54/1.47 | 2.01 | 2.72 | 51.4 | 171.4 | 800 |
| Example 5 | E | 18.2 | 18.7 | 10.9 | 13.7 | 37.6 | 1/1.02/0.93 | 1.95 | 0.91 | 51.3 | 151.8 | 600 |
| Example 6 | F | 21.8 | 35.5 | 7.4 | 8.0 | 26.0 | 1/1.62/0.53 | 2.15 | 0.33 | 34.0 | 134.8 | 800 |
| Example 7 | G | 24.6 | 40.5 | 8.7 | 5.3 | 19.4 | 1/1.64/0.55 | 2.19 | 0.34 | 24.7 | 131.4 | 800 |
| Reference Example 1 | H1 | 18.0 | 19.8 | 58.3 | 0.1 or less | 0.1 or less | (1/1.10/5.05), substantially, 1/1.10/0.93 | 2.03 | 0.85 | Instead, 47.6 of γ-alumina added | 100.2 | 800 |
| Reference Example 2 | H2 | | | | | | | | | | | 600 |
| Reference Example 3 | H3 | | | | | | | | | | | 400 |
| Reference Example 4 | I | 18.2 | 18.7 | 10.9 | 13.7 | 37.6 | 1/1.02/0.93 | 1.95 | 0.91 | 51.3 | 151.8 | 400 |
| Reference Example 5 | J | 20.2 | — | 22.6 | 14.9 | 40.1 | 1.0/—/1.75 | — | — | 55.0 | 193.5 | 800 |

Capabilities of copper-based catalysts obtained by reducing the copper-based catalyst precursor of the present invention for producing aldehyde compounds using the isomerization of a compound having a β,γ-unsaturated alcohol portion, more specifically, capabilities for producing 7-octenal from 2,7-octadiene-1-ol in the fixed-bed reaction method in which the copper-based catalyst precursors prepared in Examples 1 to 7 will be described in more detail in Assessment Examples 1 to 7.

In addition, in Comparative Assessment Examples 1 to 5, capabilities for producing 7-octenal in the fixed-bed reaction method in which the copper-based catalyst obtained by reducing the copper-based catalyst precursor outside the scope of the present invention is used will be described.

Assessment Example 1

50 mL of a mixture obtained by diluting a copper-based catalyst precursor A to 50% by mass using soda glass beads having a diameter in a range of 3.962 mm to 4.699 mm was loaded into an atmospheric pressure circulation-type stainless steel SUS316 vertical straight reaction tube (inner diameter: 22 mm, length: 1 m) including an electric heater for controlling the temperature of a catalyst layer outside, a thermocouple for measuring the temperature of the catalyst layer maintained in a range of 200±5° C. The reaction was caused at the atmospheric pressure for 3 hours, and the quantity of the product was determined through gas chromatography every 30 minutes.

The conversion ratio of 2,7-octadiene-1-ol was computed using Equation 1 described below. The unit of individual amounts in the equation is 'mol/hr'.

The conversion ratio (%) of 2,7-octadiene-1-ol={(the amount of raw materials supplied−the amount of unreacted raw materials)/the amount of raw materials supplied}×100  (Equation 1)

Examples of the respective products include 7-octenal, 2,7-octadiene-1-al, 7-octene-1-ol, octadienes, cis- or trans-6-octenal, 1-octanal, and 1-octanol. The selectivity into the above-described products was computed using Equation 2 described below. The unit of individual amounts in the equation is 'mol/hr'.

The selectivity (%) of each product={the amount of each product/(the amount of raw materials supplied−the amount of unreacted raw materials)}×100  (Equation 2)

The selectivity into high-boiling point products, the quantities of which could not be determined through gas chroma tography, was computed using Equation 3 described below. The unit of individual amounts in the equation is 'mol/hr'.

The selectivity (%) of the high-boiling point product=100−(the sum of the selectivity of individual products) (Equation 3)

During 3 hours of the reaction, there was no large change in the reaction achievement, and thus the conversion ratio and selectivity were computed from the 3-hour average composition.

Assessment Example 2

An assessment was carried out in the same manner as in Assessment Example 1 except for the fact that the copper-based catalyst precursor B was used, and the weight of the copper-based catalyst precursor B included in the diluted mixture was set to 23.4 g. During 3 hours of the reaction, there was no large change in the reaction achievement, and thus the conversion ratio and selectivity were computed from the 3-hour average composition.

Assessment Example 3

An assessment was carried out in the same manner as in Assessment Example 1 except for the fact that the copper-based catalyst precursor C was used, and the weight of the copper-based catalyst precursor C included in the diluted mixture was set to 26.5 g. During 3 hours of the reaction, there was no large change in the reaction achievement, and thus the conversion ratio and selectivity were computed from the 3-hour average composition.

Assessment Example 4

An assessment was carried out in the same manner as in Assessment Example 1 except for the fact that the copper-based catalyst precursor D was used, and the weight of the copper-based catalyst precursor D included in the diluted mixture was set to 26.5 g. During 3 hours of the reaction, there was no large change in the reaction achievement, and thus the conversion ratio and selectivity were computed from the 3-hour average composition.

Assessment Example 5

An assessment was carried out in the same manner as in Assessment Example 1 except for the fact that the copper-based catalyst precursor E was used, and the weight of the copper-based catalyst precursor E included in the diluted mixture was set to 21.4 g. During 3 hours of the reaction, there was no large change in the reaction achievement, and thus the conversion ratio and selectivity were computed from the 3-hour average composition.

Assessment Example 6

An assessment was carried out in the same manner as in Assessment Example 1 except for the fact that the copper-based catalyst precursor F was used, and the weight of the copper-based catalyst precursor F included in the diluted mixture was set to 26.5 g. During 3 hours of the reaction, there was no large change in the reaction achievement, and thus the conversion ratio and selectivity were computed from the 3-hour average composition.

Assessment Example 7

An assessment was carried out in the same manner as in Assessment Example 1 except for the fact that the copper-based catalyst precursor G was used, and the weight of the copper-based catalyst precursor G included in the diluted mixture was set to 26.5 g. During 3 hours of the reaction, there was no large change in the reaction achievement, and thus the conversion ratio and selectivity were computed from the 3-hour average composition.

Comparative Assessment Example 1

An assessment was carried out in the same manner as in Assessment Example 1 except for the fact that the copper-based catalyst precursor H1 was used, and the weight of the copper-based catalyst precursor H1 included in the diluted mixture was set to 26.6 g. During 3 hours of the reaction, there was no large change in the reaction achievement, and thus the conversion ratio and selectivity were computed from the 3-hour average composition.

Comparative Assessment Example 2

An assessment was carried out in the same manner as in Assessment Example 1 except for the fact that the copper-based catalyst precursor H2 was used, and the weight of the copper-based catalyst precursor H2 included in the diluted mixture was set to 26.0 g. During 3 hours of the reaction, there was no large change in the reaction achievement, and thus the conversion ratio and selectivity were computed from the 3-hour average composition.

Comparative Assessment Example 3

An assessment was carried out in the same manner as in Assessment Example 1 except for the fact that the copper-based catalyst precursor H3 was used, and the weight of the copper-based catalyst precursor H3 included in the diluted mixture was set to 26.0 g. During 3 hours of the reaction, the conversion ratio of 2,7-octadiene-1-ol was decreased over time. The conversion ratio became 65.3% immediately after the reaction, 64.0% 1 hour after the reaction, 63.7% 2 hours after the reaction, and 62.2% 3 hour after the reaction. The average value (63.8%) thereof was used as the conversion ratio. Meanwhile, there was no large change in the selectivity.

Comparative Assessment Example 4

An assessment was carried out in the same manner as in Assessment Example 1 except for the fact that the copper-based catalyst precursor I was used, and the weight of the copper-based catalyst precursor I included in the diluted mixture was set to 23.3 g. During 3 hours of the reaction, the conversion ratio of 2,7-octadiene-1-ol was decreased over time. The conversion ratio became 50.1% immediately after the reaction, 49.1% 1 hour after the reaction, 48.4% 2 hours after the reaction, and 47.1% 3 hour after the reaction. The average value (48.7%) thereof was used as the conversion ratio. Meanwhile, there was no large change in the selectivity.

Comparative Assessment Example 5

An assessment was carried out in the same manner as in Assessment Example 1 except for the fact that the copper-based catalyst precursor J was used, and the weight of the copper-based catalyst precursor J included in the diluted mixture was set to 26.5 g. During 3 hours of the reaction, there was no large change in the reaction achievement, and thus the conversion ratio and selectivity were computed from the 3-hour average composition.

Table 2 describes the isomerization reaction results of 2,7-octadiene-1-ol as β,γ-unsaturated alcohol compounds for which the copper-based catalyst obtained by reducing the copper-based catalyst precursors prepared in Examples 1 to 7 and Reference Examples 1 to 5 were used (Assessment Examples 1 to 7 and Comparative Assessment Examples 1 to 5).

The loading amounts in the table are the weights of the respective copper-based catalyst precursors included in 50 mL of the catalyst layer diluted to 50% by mass using the soda glass beads having a diameter in a range of 3.962 mm to 4.699 mm.

7-octenal, 2,7-octadienal, 7-octene-1-ol, octadienes, cis- or trans-6-octenal, 1-octanal, 1-octanol, and other high-boiling point compounds are referred to shortly as 7-OEL, ODL, OEA, OD, 6-OEL, OL, OA, and HB respectively.

catalyst precursor B to which calcium silicate was added was used rather than the copper-based catalyst precursor H1 to which γ-alumina was added.

According to the comparison between Assessment Example 3 and Comparative Assessment Example 5, in the copper-based catalyst precursor J including no iron, a high conversion ratio and high selectivity could not be achieved.

Particularly, when the copper-based catalyst precursors A, F, and G were used, a higher conversion ratio and a higher selectivity could be achieved. Assessment Examples 1, 6, and 7 had almost the same Cu/Fe/Al atomic ratio as the copper-based catalyst precursor A, but had different amount of calcium silicate.

The fact that sufficient performance can be achieved even by forming the copper-based catalyst precursor of the present invention will be described. A method for forming the copper-

TABLE 2

| | Copper-based catalyst precursor | Loading amount (g) | Conversion ratio (%) | Selectivity into various compounds (%) | | | | | | | |
|---|---|---|---|---|---|---|---|---|---|---|---|
| | | | | 7-OEL | ODL | OEA | OD | 6-OEL | OL | OA | HB |
| Assessment Example 1 | A | 26.5 | 96.4 | 81.5 | 9.8 | 4.7 | 1.0 | 1.3 | 1.3 | 0.2 | 0.2 |
| Assessment Example 2 | B | 23.4 | 92.2 | 79.4 | 10.7 | 5.6 | 0.3 | 1.1 | 0.8 | 0.2 | 1.9 |
| Assessment Example 3 | C | 26.5 | 92.4 | 78.1 | 10.8 | 5.5 | 1.1 | 1.2 | 1.1 | 0.3 | 1.9 |
| Assessment Example 4 | D | 26.5 | 92.5 | 76.6 | 11.1 | 6.2 | 1.0 | 1.2 | 0.7 | 0.2 | 3.0 |
| Assessment Example 5 | E | 21.4 | 91.8 | 76.6 | 10.8 | 5.1 | 0.5 | 1.2 | 1.3 | 0.3 | 4.2 |
| Assessment Example 6 | F | 26.5 | 97.8 | 81.3 | 9.6 | 4.6 | 1.1 | 1.3 | 1.4 | 0.2 | 0.6 |
| Assessment Example 7 | G | 26.5 | 95.2 | 81.1 | 10.1 | 5.8 | 0.6 | 0.9 | 0.7 | 0.2 | 0.6 |
| Comparative Assessment Example 1 | H1 | 26.6 | 82.3 | 75.8 | 10.8 | 5.1 | 1.3 | 1.3 | 1.6 | 0.3 | 3.8 |
| Comparative Assessment Example 2 | H2 | 26.0 | 79.3 | 75.0 | 12.6 | 6.3 | 0.4 | 1.4 | 1.3 | 0.3 | 2.7 |
| Comparative Assessment Example 3 | H3 | 26.1 | 63.8 | 72.8 | 14.5 | 6.2 | 0.6 | 1.9 | 1.9 | 0.4 | 1.7 |
| Comparative Assessment Example 4 | I | 23.3 | 48.7 | 73.5 | 14.8 | 7.5 | 0.6 | 1.2 | 0.9 | 0.4 | 1.1 |
| Comparative Assessment Example 5 | J | 26.5 | 78.2 | 68.2 | 12.9 | 7.0 | 5.5 | 1.2 | 1.4 | 0.3 | 3.5 |

The comparison between Assessment Examples 2 and 5 and Comparative Assessment Example 4 exhibited a difference in the calcination temperature of the dried product of the same coprecipitated mixture, and in the copper-based catalyst precursor B calcined at 800° C., the copper-based catalyst precursor E calcined at 600° C., and the copper-based catalyst precursor I calcined at 400° C., a high conversion ratio and high selectivity could be achieved only in a case in which the copper-based catalyst precursor for which the calcination temperature was set to 600° C. or higher was used. The above-described improvement of the catalyst performance by the high-temperature calcination could be confirmed even in a case in which the copper-based catalyst precursors H1 to H3 to which γ-alumina was added were used (Comparative Assessment Examples 1 to 3). However, according to the comparison between Assessment Example 2 and Comparative Assessment Example 1, a higher conversion ratio and a higher selectivity could be achieved when the copper-based catalyst precursor will be described in Examples 8 and 9. In Assessment Examples 8 and 9, capabilities of a copper-based catalyst obtained by reducing the formed copper-based catalyst precursor for isomerizing an aldehyde compound from a compound having a β,γ-unsaturated alcohol portion, more specifically, capabilities for isomerizing 7-octenal from 2,7-octadiene-1-ol in the fixed-bed reaction method in which the copper-based catalyst precursors prepared in Examples 8 and 9 are used will be described in more detail.

Example 8

The dried product of the coprecipitated mixture prepared under the same conditions as in Example 1 was formed into a cylindrical shape having a diameter of 3 mm and a thickness of 3 mm using a rotary tablet forming machine. The formed product was calcined in the air at 800° C. for 6 hours, thereby obtaining a catalyst precursor K.

Example 9

The powder-form copper-based catalyst precursor prepared under the same conditions as in Example 1 was formed into a cylindrical shape having a diameter of 3 mm and a thickness of 3 mm using a rotary tablet forming machine. After that, the formed product was calcined at 500° C. for 1 hour, thereby obtaining a catalyst precursor L.

Assessment Example 8

An assessment was carried out using the same method as in Assessment Example 1 except for the fact that 50 mL of a mixture obtained by diluting the catalyst precursor K to 50% by mass using soda glass beads having a diameter in a range of 3.962 mm to 4.699 mm was loaded. The mass of the copper-based catalyst precursor included in the diluted mixture was set to 26.9 g.

During 3 hours of the reaction, there was no large change in the reaction achievement, and thus the conversion ratio and selectivity were computed from the 3-hour average composition.

Assessment Example 9

An assessment was carried out using the same method as in Assessment Example 1 except for the fact that 50 mL of a mixture obtained by diluting the catalyst precursor L to 50% by mass using soda glass beads having a diameter in a range of 3.962 mm to 4.699 mm was loaded. The mass of the copper-based catalyst precursor included in the diluted mixture was set to 26.9 g.

During 3 hours of the reaction, there was no large change in the reaction achievement, and thus the conversion ratio and selectivity were computed from the 3-hour average composition.

In Assessment Examples 8 and 9 in Table 3, the isomerization reaction results of 2,7-octadiene-1-ol as β,γ-unsaturated alcohol compounds for which the copper-based catalyst obtained by reducing the formed copper-based catalyst precursors prepared in Examples 8 and 9 is used are described. In addition, the result of Assessment Example 1 in which the powder-form copper-based catalyst precursor was used is also described for reference.

steel SUS316 vertical straight reaction tube (inner diameter: 22 mm, length: 1 m) including an electric heater for controlling the temperature of a catalyst layer outside, a thermocouple for measuring the temperature of the catalyst layer inside, a gas supply opening in the upper portion, and a sampling opening in the lower portion.

In a state in which the temperature of the catalyst layer was maintained in a range of 200±5° C., the air was circulated at 24 L/hr for 1 hour. After that, the supply of the air was stopped, and nitrogen gas was circulated at 275.0 L/hr for 1 hour so that the temperature of the catalyst layer was maintained in a range of 200±5° C. After that, the flow rate of hydrogen gas was increased while the flow rate of nitrogen gas was decreased so that the temperature of the catalyst layer was maintained in a range of 200±5° C., finally, the flow rate of hydrogen gas was set to 12 L/hr, and the copper-based catalyst precursor A was reduced over 1 hour.

After the reduction treatment, the supply of the hydrogen gas was temporarily stopped, and a gas mixture of 0.3% by volume of hydrogen and 99.7% by volume of nitrogen and a liquid mixture of 30.4% by mass of 7-octene-1-ol and 69.6% by mass of 2,7-octadiene-1-ol were respectively supplied at 101.8 L/hr and 53.1 g/hr so that the temperature of the catalyst layer was maintained in a range of 200±5° C. The reaction was caused at 0.145 MPa (G) for 4 hours.

During 4 hours of the reaction, there was no large change in the reaction achievement. The 4-hour average composition was 0.3% by mass of 2,7-octadiene-1-ol, 79.6% by mass of 7-octenal, 0.1% by mass of 2,7-octadienal, 15.3% by mass of 7-octene-1-ol, 0.2% by mass of octadienes, 0.1% by mass of cis- or trans-6-octenal, 3.5% by mass of 1-octanal, 0.7% by mass of 1-octanol, and 0.2% by mass of other high-boiling point compounds.

Comparative Assessment Example 6

An assessment was carried out using the same operation and the same method as in Assessment Example 10 except for the fact that 100 mL of "E26L" manufactured by JGC Catalysts and Chemicals Ltd. was used instead of the use of 100 mL of the copper-based catalyst precursor L.

TABLE 3

| | Copper-based catalyst precursor | Note of copper-based catalyst precursor | Loading amount (g) | Conversion ratio (%) | Selectivity into various compounds (%) | | | | | | | |
|---|---|---|---|---|---|---|---|---|---|---|---|---|
| | | | | | 7-OEL | ODL | OEA | OD | 6-OEL | OL | OA | HB |
| Assessment Example 8 | K | Precursor obtained by molding the dried raw powder of A and then calcining the powder at 800° C. | 26.9 | 80.1 | 81.0 | 9.1 | 5.2 | 1.9 | 1.2 | 1.4 | 0.2 | — |
| Assessment Example 9 | L | Precursor obtained by molding catalyst precursor A | 26.9 | 94.6 | 82.0 | 8.5 | 4.6 | 1.2 | 1.5 | 1.9 | 0.2 | — |
| Assessment Example 1 | A | Powder-form copper-based catalyst precursor fired at 800° C. | 26.5 | 96.4 | 81.5 | 9.8 | 4.7 | 1.0 | 1.3 | 1.3 | 0.2 | 0.2 |

As described in Assessment Examples 1 to 9, the copper-based catalyst precursor of the present invention can be used for the isomerization of the β,γ-unsaturated alcohol compound in both a powder state and a formed state.

Assessment Example 10

Isomerization Reaction in the Presence of Hydrogen Gas and Nitrogen Gas 100 mL of the copper-based catalyst precursor L was loaded into an atmospheric pressure circulation-type stainless During 4 hours of the reaction, there was no large change in the reaction achievement. The 4-hour average composition was 0.3% by mass of 2,7-octadiene-1-ol, 71.7% by mass of 7-octenal, 0.1% by mass of 2,7-octadienal, 18.5% by mass of 7-octene-1-ol, 1.0% by mass of octadienes, 0.1% by mass of cis- or trans-6-octenal, 2.9% by mass of 1-octanal, 0.7% by mass of 1-octanol, and 4.7% by mass of other high-boiling point compounds.

As clarified from the comparison between Assessment Example 10 in which the copper-based catalyst precursor L was used and Comparative Assessment Example 6 in which "E26L" was used, even in a case in which the isomerization reaction was caused in the co-presence of hydrogen gas, the yield of 7-octenal became higher when the copper-based catalyst precursor L was used.

The copper-based catalyst precursor of the present invention can be used for the hydrogenation of a carbon-carbon double bond, the hydrogenation of a carbon-oxygen double bond, and the like which are the ordinary uses of the copper-based catalyst precursor. More specifically, in Examples 10 and 11 described below, the hydrogenation reaction of 1-octanol from 7-octenal in the slurry-bed reaction method in which the copper-based catalyst precursor was used will be described.

Example 10

0.3 g of the catalyst precursor A and 20 g of dehydrated and distilled 1,4-dioxane were put in a 100 mL SUS316 autoclave, were substituted by nitrogen, and were put at the atmospheric pressure. After that, in a state in which the components were sufficiently stirred, the catalyst precursor A was reduced for 30 minutes in a state of 180° C. and a hydrogen pressure of 10 MPa (G). While this state is maintained, 40 g (0.317 mol) of 7-octenal was sent by pressure, and a reaction was initiated.

The amount of the product after 5 hours of the reaction was determined through gas chromatography. After 5 hours of the reaction, the amount of 7-octenal was equal to or less than the detection capability, and as the products, only 7-octene-1-ol and 1-octanol can be detected. The yields of these products were computed using Formula 4 described below. The units of the respective amounts in the formula are "mol".

Yield (%) of each product=(the amount of each product/introduced 7-octenal)×100    (Equation 4)

The yield of 7-octene-1-ol after 5 hours of the reaction was 2.4%, and the yield of 1-octanol was 97.6%.

Example 11

The same reaction was caused as in Example 10 except for the fact that 0.3 g of the catalyst precursor B was used. After 5 hours of the reaction, the amount of 7-octenal was equal to or less than the detection capability, and the yield of 7-octene-1-ol was 6.4%, and the yield of 1-octanol was 93.6%.

As described in Examples 10 and 11, the copper-based catalyst precursor of the present invention can be used even for the hydrogenation of a carbon-carbon double bond and a carbon-oxygen double bond.

The copper-based catalyst precursor of the present invention can be used for the hydrogenation of ketone compounds having a carbon-oxygen double bond. More specifically, in Example 12 described below, the hydrogenation reaction of 4-methyl-2-pentanol from 4-methyl-2-pentanone in the slurry-bed reaction method in which the copper-based catalyst precursor was used will be described.

Example 12

A reaction was caused using the same method as in Example 10 except for the fact that 40 g (0.399 mol) of 4-methyl-2-pentanone was used instead of 7-octenal. After 40 minutes, the reaction liquid contained 40.31 g of 4-methyl-2-pentanol, and the yield thereof was 98.8%.

As described in Example 12, the copper-based catalyst precursor of the present invention can also be used for the hydrogenation of ketone compounds having a carbon-oxygen double bond.

INDUSTRIAL APPLICABILITY

The copper-based catalyst precursor of the present invention is useful as a catalyst for the reaction of a compound having a β,γ-unsaturated alcohol portion for isomerizing the β,γ-unsaturated alcohol portion to an aldehyde group. For example, 7-octenal obtained by isomerizing 2,7-octadiene-1-ol using the copper-based catalyst precursor is a compound having a highly reactive terminal double bond and an aldehyde group, and is useful as a raw material for a variety of industrial chemicals. Specifically, 1,9-nonanedial can be produced by hydroformylating 7-octenal, and furthermore, it is possible to obtain 1,9-nonanediamine which is useful as a macromolecular monomer raw material through a reductive amination reaction.

Furthermore, the copper-based catalyst precursor of the present invention is also useful as a hydrogenation catalyst for compounds having either or both a carbon-carbon double bond and a carbon-oxygen double bond. Particularly, 1-octanol obtained through the hydrogenation reaction of 7-octenal is useful as a resin plasticizer.

The invention claimed is:

1. A copper-based catalyst precursor, obtained by a process comprising: calcining a mixture comprising copper, iron, aluminum, and calcium silicate,
   wherein
   an atomic ratio of iron and aluminum to copper [(Fe+Al)/Cu] is in a range of from 1.71 to 2.5,
   an atomic ratio of aluminum to iron [Al/Fe] is in a range of from 0.001 to 3.3, and
   the mixture comprises calcium silicate in a range of from 15% by mass to 65% by mass at a temperature of from 500° C. to 1,000° C.

2. The copper-based catalyst precursor according to claim 1,
   wherein
   the mixture is a dried product of a coprecipitated mixture obtained by a process comprising: mixing a coprecipitate and calcium silicate, and
   the coprecipitate is obtained by reacting a mixed aqueous solution comprising a water-soluble copper salt, a water-soluble iron salt, and a water-soluble aluminum salt with a basic aqueous solution.

3. The copper-based catalyst precursor according to claim 1,
   wherein, in the calcium silicate, an atomic ratio of silicon to calcium [Si/Ca] is in a range of from 0.5 to 6.5.

4. The copper-based catalyst precursor according to claim 2,
   wherein a BET specific surface area of the mixture is in a range of from 50 $m^2$/g to 250 $m^2$/g.

5. The copper-based catalyst precursor according to claim 1,
   wherein the calcium silicate is a Gyrolite-type synthetic calcium silicate represented by $2CaO \cdot 3SiO_2 \cdot mSiO_2 \cdot nH_2O$ where m and n, respectively, are numbers satisfying 1<m<2 and 2<n<3.

6. The copper-based catalyst precursor according to claim 5,
   wherein a bulk specific volume of the calcium silicate is 4 mL/g or more.

7. A copper-based catalyst obtained by a process comprising: reducing the copper-based catalyst precursor according to claim 1.

8. A method for producing the copper-based catalyst precursor according to claim 1, the method comprising:
   reacting a mixed aqueous solution comprising a water-soluble copper salt, a water-soluble iron salt, and a water-soluble aluminum salt with a basic aqueous solution to obtain a coprecipitate comprising copper, iron, and aluminum;
   adding calcium silicate to a suspension comprising the coprecipitate suspended in water and mixing calcium silicate and the suspension to obtain a coprecipitated mixture;
   separating the coprecipitated mixture, washing the coprecipitated mixture with water, and then drying the coprecipitated mixture, thereby obtaining a dried product of the coprecipitated mixture; and
   calcining the dried product of the coprecipitated mixture at a calcination temperature of from 500° C. to 1,000° C.

9. The method according to claim 8,
wherein,
in said reacting, a reaction temperature is in a range of from 5° C. to 150° C., and a pH of the aqueous solution is in a range of from 6.0 to 13.5, and
in said adding, calcium silicate is added to the suspension at a temperature of from 5° C. to 100° C., and a pH of the suspension is in a range of from 7 to 9.

10. The method according to claim 8,
wherein, in said reacting, the water-soluble copper salt is copper (II) sulfate, the water-soluble iron salt is iron (I) sulfate, and the water-soluble aluminum salt is aluminum sulfate.

11. The method according to claim 8,
wherein the calcination temperature in said calcining is in a range of from 600° C. to 900° C.

12. A hydrogenation method of a compound comprising at least one of a carbon-carbon double bond and a carbon-oxygen double bond, the method comprising:
   employing the copper-based catalyst precursor according to claim 1 in the method.

13. The hydrogenation method according to claim 12,
wherein the method is carried out at a temperature of from 100° C. to 300° C. and at a total pressure of from 0.01 MPa(G) to 30 MPa(G).

14. The hydrogenation method according to claim 12,
wherein the method is carried out using a slurry-bed reaction method.

15. The hydrogenation method according to claim 12,
wherein the compound comprising at least one of a carbon-carbon double bond and a carbon-oxygen double bond is selected from the group consisting of an aldehyde which optionally comprises a carbon-carbon double bond, a ketone which optionally comprises a carbon-carbon double bond, a carboxylic acid which optionally comprises a carbon-carbon double bond, an ester which optionally comprises a carbon-carbon double bond, an acid anhydride which optionally comprises a carbon-carbon double bond, and a sugar which optionally comprises a carbon-carbon double bond.

* * * * *